(12) United States Patent
Pettersson-Falk

(10) Patent No.: US 12,399,042 B2
(45) Date of Patent: Aug. 26, 2025

(54) DATA LOGGER UNIT, SENSOR UNIT, ABSORBENT ARTICLE MANAGEMENT SYSTEM AND IDENTIFICATION METHOD

(71) Applicant: Essity Hygiene and Health Aktiebolag, Gothenburg (SE)

(72) Inventor: Henrik Pettersson-Falk, Harryda (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 712 days.

(21) Appl. No.: 17/439,993

(22) PCT Filed: Apr. 15, 2019

(86) PCT No.: PCT/EP2019/059672
§ 371 (c)(1),
(2) Date: Sep. 16, 2021

(87) PCT Pub. No.: WO2020/211922
PCT Pub. Date: Oct. 22, 2020

(65) Prior Publication Data
US 2022/0170874 A1 Jun. 2, 2022

(51) Int. Cl.
*G01D 9/00* (2006.01)
*A61F 13/42* (2006.01)
*G01N 27/22* (2006.01)

(52) U.S. Cl.
CPC ............ *G01D 9/005* (2013.01); *A61F 13/42* (2013.01); *G01N 27/221* (2013.01); *A61F 2013/424* (2013.01)

(58) Field of Classification Search
CPC ........ G01D 9/005; G01D 21/00; A61F 13/42; A61F 2013/424; A61F 13/15; G01N 27/221; G01N 27/223
See application file for complete search history.

(56) References Cited

U.S. PATENT DOCUMENTS

| 5,845,644 A | 12/1998 | Hughes et al. |
| 7,667,608 B2 | 2/2010 | Ales et al. |

(Continued)

FOREIGN PATENT DOCUMENTS

| CN | 1402768 A | 3/2003 |
| CN | 102481112 A | 5/2012 |

(Continued)

OTHER PUBLICATIONS

Colombian Application No. NC2021/0013791; Office Action with English translation dated Sep. 2, 2024; 38 pages.

(Continued)

*Primary Examiner* — Daryl C Pope
(74) *Attorney, Agent, or Firm* — CANTOR COLBURN LLP

(57) ABSTRACT

The present invention relates to data logger units, sensor units, and in particular those which are suitable for sensing the hygienic state of an absorbent article. The present disclosure also relates to a method of identifying a sensor unit for an absorbent article performed by a data logger unit adapted to cooperate with the sensor unit, as well as an absorbent article management system. The data logger unit and the sensor have identification terminals. A characteristic property of the sensor unit is encoded in the potentials at each of the identification terminals. The data logger unit can decode the potentials at each of the identification terminals to determine the characteristic property of a connected sensor unit.

43 Claims, 15 Drawing Sheets

(56) References Cited

U.S. PATENT DOCUMENTS

| | | | |
|---|---|---|---|
| 8,663,106 B2* | 3/2014 | Stivoric | G16H 40/63 |
| | | | 600/301 |
| 8,816,149 B2 | 8/2014 | Richardson et al. | |
| 9,904,562 B2 | 2/2018 | Bergström et al. | |
| 11,173,073 B2 | 11/2021 | Macnaughton et al. | |
| 2004/0078219 A1 | 4/2004 | Kaylor et al. | |
| 2005/0156744 A1 | 7/2005 | Pires | |
| 2005/0245839 A1 | 11/2005 | Stivoric et al. | |
| 2007/0083174 A1 | 4/2007 | Ales et al. | |
| 2007/0252713 A1 | 11/2007 | Rondoni et al. | |
| 2008/0132859 A1 | 6/2008 | Pires | |
| 2008/0171920 A1 | 7/2008 | Teller et al. | |
| 2008/0269702 A1 | 10/2008 | Ales et al. | |
| 2010/0245114 A1 | 9/2010 | Celik-Butler et al. | |
| 2012/0149996 A1 | 6/2012 | Stivoric et al. | |
| 2012/0268278 A1 | 10/2012 | Lewis et al. | |
| 2013/0018340 A1 | 1/2013 | Abraham et al. | |
| 2013/0268231 A1 | 10/2013 | Sato | |
| 2013/0303867 A1 | 11/2013 | Elfstrom et al. | |
| 2013/0307570 A1 | 11/2013 | Bosaeus et al. | |
| 2014/0218057 A1 | 8/2014 | White et al. | |
| 2014/0350503 A1 | 11/2014 | Bosaeus et al. | |
| 2014/0371702 A1 | 12/2014 | Bosaeus et al. | |
| 2016/0080841 A1 | 3/2016 | Bergström et al. | |
| 2016/0361209 A1 | 12/2016 | Mashin-Chi et al. | |
| 2017/0307458 A1 | 10/2017 | Landmann | |
| 2018/0333306 A1 | 11/2018 | Ahong et al. | |
| 2019/0247650 A1 | 8/2019 | Tran | |
| 2020/0060899 A1 | 2/2020 | Neeley et al. | |
| 2020/0323285 A1 | 10/2020 | Longinotti-Buitoni et al. | |
| 2020/0352794 A1 | 11/2020 | Curran et al. | |
| 2021/0113130 A1 | 4/2021 | Tran | |
| 2022/0015956 A1 | 1/2022 | Öberg et al. | |
| 2022/0054326 A1 | 2/2022 | Øberg et al. | |

FOREIGN PATENT DOCUMENTS

| | | |
|---|---|---|
| CN | 102573713 A | 7/2012 |
| CN | 103269667 A | 8/2013 |
| CN | 103269668 A | 8/2013 |
| CN | 103327944 A | 9/2013 |
| CN | 103561705 A | 2/2014 |
| CN | 104066409 A | 9/2014 |
| CN | 107530214 A | 1/2018 |
| CO | 08070222 | 11/2008 |
| EP | 1995579 A2 | 11/2008 |
| EP | 3415130 A1 | 12/2018 |
| JP | S48123527 | 10/1973 |
| JP | S50069190 U | 6/1975 |
| JP | 2000093448 A | 4/2000 |
| JP | 2002082080 A | 3/2002 |
| JP | 2009006180 A | 1/2009 |
| JP | 2009031264 A | 2/2009 |
| JP | 2013039158 A | 2/2013 |
| JP | 2013218454 A | 10/2013 |
| JP | 2018501864 A | 1/2018 |
| KR | 101667120 B1 | 10/2016 |
| WO | 2006047815 A1 | 5/2006 |
| WO | 2007128038 A1 | 11/2007 |
| WO | 2010049827 A2 | 5/2010 |
| WO | 2010123425 A1 | 10/2010 |
| WO | 2011004165 A1 | 1/2011 |
| WO | 2011054045 A1 | 5/2011 |
| WO | 2012084924 A1 | 6/2012 |
| WO | 2012084987 A2 | 6/2012 |
| WO | 2012114208 A1 | 8/2012 |
| WO | 2012166765 A1 | 12/2012 |
| WO | 2015102084 A1 | 7/2015 |
| WO | 2016090492 A1 | 6/2016 |
| WO | 2017152687 A1 | 9/2017 |
| WO | 2019096413 A1 | 5/2019 |
| WO | 2020125999 A1 | 6/2020 |
| WO | 2020126000 A1 | 6/2020 |
| WO | 2021004598 A1 | 1/2021 |
| WO | 2024061465 A1 | 3/2024 |

OTHER PUBLICATIONS

Third Party Observation for European Application No. EP20180826035 dated Apr. 28, 2023 15:01; 9 pages.
Third Party Observation for European Application No. EP20180826035 dated Apr. 28, 2023 15:05; 6 pages.
Third Party Observation for European Application No. EP20180826035 dated Mar. 19, 2024 11:42; 9 pages.
Third Party Observation for European Application No. EP20180826035 dated Mar. 19, 2024 14:42; 2 pages.
Third Party Submission on European Application No. 3897496A1 filed on Apr. 28, 2023; 16 pages.
Third Party Submission on European Application No. EP3897496A1 dated Apr. 27, 2023; 22 pages.
Japanese Application No. 2021-531773; Office Action with English Translation dated Nov. 14, 2022; 9 pages.
Korean Application No. 10-2021-7018888; Korean Office Action with English Translation dated Dec. 12, 2022; 18 pages.
Canadian Application No. 3,119,685; Canadian Office Action dated May 5, 2023; 4 pages.
Chinese Application No. 201880100107.X; Office Action with English Translation dated Mar. 25, 2023; 19 pages.
Colombian Application No. NC2021/0006510; Colombian Office Action with English translation dated Mar. 15, 2023; 28 pages.
Colombian Application No. NC2021/0006510; Colombian Office Action with English translation dated Nov. 25, 2022; 18 pages.
European Application No. 18826035.0; Third Party Observation filed Apr. 27, 2023; 22 pages.
European Application No. 18826035.0; Third Party Observation filed Apr. 28, 2023; 6 pages.
European Application No. 18826035.0; Third Party Observation filed Apr. 28, 2023; 9 pages.
Japanese Application No. 2021-531773; Decision to Grant with English Translation dated Feb. 14, 2023; 6 pages.
Japanese Application No. 2021-535834; Japanese Office Action with English translation mailed Mar. 27, 2023; 11 pages.
Korean Application No. 10-2021-7018888; Korean Office Action with English Translation dated Jun. 20, 2023; 3 pages.
Korean Application No. 10-2021-7019765; Korean Office Action with English Translation dated May 19, 2023; 23 pages.
Colombian Office Action issued in Colombian Application No. NC/2021/0008642; dated Nov. 30, 2023; 14 pages.
Non-Final Office Action issued in U.S. Appl. No. 17/413,669 dated Mar. 13, 2024; 14 pages.
National Intellectual Property Administration (CNIPA) of the People's Republic of China, Notification of the First Office Action, Application No. 201880100107.X, dated Dec. 2, 2021 (15 pages).
European Application No. 18826354.5-1102; Communication pursuant to Article 94(3) EPC dated Oct. 20, 2023; 3 pages.
Japanese Application No. 2021-535834; Decision of Rejection dated Aug. 21, 2023; 4 pages.
Japanese Application No. 2021-535834; Decision to Reject the Amendments dated Aug. 21, 2023; 9 pages.
Japanese Application No. 2021-560984; Decision of Rejection dated May 29, 2023; 8 pages.
Final Office Action issued in U.S. Appl. No. 17/413,670 dated Jun. 27, 2024.
Chinese Office Action issued in Chinese Application No. 201980095471.6 dated Dec. 13, 2023; 31 pages.
Non-Final Office Action issued in U.S. Appl. No. 17/413,670 dated Feb. 16, 2024, 63 pages.
Brazilian Search Report issued in Brazilian Application No. BR112021018767-7 dated Mar. 20, 2024.
Colombia Office Action issued in Application No. NC2021/0013791 dated Mar. 1, 2024 with English translation.
Notification of Grounds for Refusal issued in Korean Application No. 10-2021-7036456 forwarding date Mar. 22, 2024 with English translation.

(56) References Cited

OTHER PUBLICATIONS

Second Office Action issued in Chinese Application No. 201980095471.6 dated May 15, 2024 with English translation.

European Patent Office, International Search Report and Written Opinion of the International Searching Authority, International Application No. PCT/EP2018/086217, mailed Mar. 20, 2019 (13 pages).

European Patent Office, International Search Report and Written Opinion of the International Searching Authority, International Application No. PCT/EP2018/086218, mailed Jun. 25, 2019 (13 pages).

European Patent Office, International Search Report and Written Opinion of the International Searching Authority, International Application No. PCT/EP2019/059672, mailed Jan. 27, 2020 (14 pages).

Australian Government, IP Australia, Examination report No. 1 for standard patent application, Application No. 2018454396, mailed Oct. 29, 2021 (4 pages).

Brazilian Application No. BR112021008140-2; Brazilian Search Report dated Sep. 7, 2022; 4 pages.

Brazilian Application No. BR112021011142-5; Brazilian Search Report dated Sep. 7, 2022; 4 pages.

Canadian Application No. 3,123,929; Canadian Office Action dated Oct. 6, 2022; 4 pages.

Canadian Application No. 3,134,131; Canadian Office Action dated Nov. 24, 2022; 4 pages.

European Application No. 18826035.0; Communication pursuant to Article 94(3) EPC dated Jan. 3, 2023; 3 pages.

International Searching Authority, Search Report and Written Opinion issued in PCT/EP2018/086217, mailed Mar. 20, 2019 (13 pages).

International Searching Authority, Search Report and Written Opinion issued in PCT/EP2018/086218, mailed Jun. 25, 2019 (13 pages).

Japanese Application No. 2021-535834; Japanese Office Action with English translation mailed Sep. 12, 2022; 12 pages.

Japanese Application No. 2021-560984; Japanese Office Action with English Translation dated Oct. 31, 2022; 14 pages.

Korean Application No. 10-2021-7019765; Korean Office Action with English Translation dated Dec. 13, 2022; 22 pages.

Chinese Application No. 201880100107.X; Chinese Office Action dated Oct. 26, 2022; 11 pages.

Canadian Application No. 3,119,685; Canadian Office Action dated Oct. 13, 2022; 6 pages.

Australian Government, IP Australia, Examination report No. 1 for standard patent application, Application No. 2018454245, mailed Oct. 22, 2021 (5 pages).

National Intellectual Property Administration (CNIPA) of the People's Republic of China, Notification of the First Office Action, Application No. 201880100095.0, dated Dec. 2, 2021 (26 pages).

Australian Application No. 2018454396; Office Action dated Mar. 15, 2022; 4 pages.

Australian Government, IP Australia, Examination report No. 1 for standard patent application, Application No. 2018454245, mailed Mar. 31, 2022 (5 pages).

Chinese Application No. 201880100107.X; Office Action dated Jun. 28, 2022; 12 pages.

National Intellectual Property Administration (CNIPA) of the People's Republic of China, Office Action, Application No. 201880100095.0, dated Aug. 10, 2022 (26 pages).

Japanese Application No. 2021-531773; Office Action with English Translation dated May 9, 2022; 11 pages.

U.S. Appl. No. 17/413,670; Non-Final Office Action dated Nov. 8, 2024; 22 pages.

Australian Application No. 2019440869; Examination Report 1 dated Dec. 18, 2024; 3 pages.

International Search Report & Written Opinion for International Application No. PCT/EP2022/076369; International Filing Date: Sep. 22, 2022; Date of Mailing: May 19, 2023; 15 pages.

Japanese Application No. 2023-138032; Office Action with English translation dated Dec. 2, 2024; 14 pages.

* cited by examiner

DATA LOGGER UNIT, SENSOR UNIT, ABSORBENT ARTICLE MANAGEMENT SYSTEM AND IDENTIFICATION METHOD

CROSS REFERENCE TO RELATED APPLICATION

The present application is a U.S. National Stage entry under 35 U.S.C. § 371 of, and claims priority to, International Application No. PCT/EP2019/059672, filed Apr. 15, 2019, the disclosure of which is hereby incorporated herein by reference in its entirety.

FIELD OF THE INVENTION

The present invention relates to data logger units, sensor units, and in particular those which are suitable for sensing the hygienic state of an absorbent article. The present disclosure also relates to a method of identifying a sensor unit for an absorbent article performed by a data logger unit adapted to cooperate with the sensor unit, as well as an absorbent article management system.

BACKGROUND OF THE INVENTION

Absorbent articles, such as diapers, absorbent underwear, sanitary products and incontinence shields require periodic replacement, in use, to ensure that the absorbency of the article is not compromised.

In many settings, including domestic settings, institutional settings, healthcare settings and the like, there is a need to monitor the state of an absorbent article provided to a user to ensure that the article contains satisfactory absorbent capacity to fulfil its function.

Conventionally, such monitoring may be performed as self-monitoring by the user, in which the user informs care staff that the capacity of the absorbent article to absorb has diminished, or by periodic checking of the absorbent article by the user or by care staff. However, such processes are labour intensive. Moreover, the information gathered about the personal needs of the user in respect of the needed frequency of replacement of the absorbent article or the needed capacity of the absorbent article is slow to aggregate, and is frequently and incompletely collected.

Accordingly, it has been proposed to provide absorbent articles with sensors, which are coupled to data logging electronics. The data logging electronics can determine the absorbent state of the absorbent article, and, for example, can notify a carer when the absorbent state of the absorbent article has reached a predetermined state.

Arrangements have been proposed which use sensing wires embedded in an absorbent core of the absorbent article, such that data logging electronics measure the resistance between the wires to determine the presence of liquid in the absorbent core, and hence the state of the absorbent article.

In some configurations, the data logger can notify the user or nearby care giver by means of appropriate visual or audible signals that liquid is present in the core and therefore that the absorbent article requires replacement.

It has also been proposed to use such logging electronics as part of an absorbent article management system. In such a system, the data logging electronics may communicate the absorbent state of the absorbent article to a remote terminal. The remote terminal can be used for monitoring the absorbent state of the absorbent article. Such management systems may be of particular utility where the users may have difficulty communicating their needs to care staff, such as in early years child care settings or in hospital settings.

In some systems, the remote terminal may aggregate the information recorded from a large number of data loggers associated with respective users. By such management systems, the absorbent state of a large number of articles associated with a large number of respective users can be conveniently monitored with reduced staffing requirements.

However, providing such articles having sensors and data logging electronics, and therefore consequently providing such systems, can be resource-intensive, in that absorbent articles fitted with such sensors and data logging electronics have a significantly higher unit cost that manually-monitored absorbent articles. This higher cost is significant because absorbent articles typically require frequent replacement, to the extent of several replacements of the article per user per day.

To address this, it has been proposed to provide data logging electronics and corresponding sensors as discrete logging packages which may be removably provided to an appropriately-designed absorbent article in order to monitor that absorbent article. When the article is replaced, then the logging package can be removed and provided to the replacement article.

However, because such sensors are difficult to integrate into the absorbent core of an absorbent article, the sensing capability may be reduced in systems using replaceable logging packages. Moreover, since absorbent articles are often provided in a range of forms and sizes, a logging package which is appropriate for provision to one type or size of absorbent article may perform poorly when used in combination of another type or size of absorbent article.

Accordingly, there is need for a more flexible means of measuring and monitoring the absorbent status of absorbent articles which overcomes at least some of the drawbacks associated with prior arrangements.

SUMMARY OF THE INVENTION

According to a first aspect of the present invention, there is provided a method of identifying, by a data logger unit, a sensor unit for an absorbent article. The sensor unit comprises a sensor-side terminal portion. The sensor unit comprises at least one sense element. The at least one sense element is electrically connected to at least one measurement terminal of the sensor-side terminal portion. The data logger unit comprises a logger-side terminal portion. The data logger unit comprises a measurement module electrically connected to at least one sense terminal of the logger-side terminal portion. The sensor terminal portion engages the logger-side terminal portion. The engagement is such as to bring terminals of the sensor-side terminal portion into electrical connection with corresponding terminals of the logger-side sensor portion. The data logger unit is adapted to perform an electrical measurement of the at least one sense element. The measurement is performed via the at least one measurement terminal of the sensor-side terminal portion. The measurement is performed via the at least one measurement terminal of the logger-side terminal portion. The data logger unit has a plurality of identification terminals at the logger-side terminal portion. The plurality of identification terminals are electrically connected to the measurement module. The sensor terminal portion has a plurality of identification terminals at the sensor-side terminal portion. The measurement module performs an electrical measurement of the plurality of identification terminals of the logger-side terminal portion. The measurement is performed to identify a characteristic property of the sensor unit. The characteristic property of the sensor unit is encoded in the electrical potentials of the identification terminals of the sensor-side terminal portion.

The sensor-side terminal portion may have a reference terminal. The logger-side terminal portion may have a reference terminal. The measurement module may provide a reference potential to the reference terminal of the logger-side terminal portion. At least one of the identification terminals of the sensor-side terminal portion may be electrically connected via a conductor of the sensor unit to the reference terminal of the sensor-side terminal portion. The characteristic property of the sensor unit may be encoded in the potential at each of the identification terminals of the sensor-side terminal portion as compared with the reference potential.

A resistor of the data logger unit may be electrically connected between each of the identification terminals of the sensor-side terminal portion and a conductor of the data logger unit maintained at a potential provided by the measurement module which is different from the reference potential.

One or more of the identification terminals of the sensor-side terminal portion may be electrically connected by a conductor of the sensor unit to the reference terminal of the sensor-side terminal portion. The remaining identification terminals of the sensor-side terminal portion may be not electrically connected to the sensor reference terminal.

The reference potential may be a ground potential of the measurement module.

The reference terminal of the sensor-side terminal portion may be a ground reference terminal. The reference terminal of the sensor-side terminal portion may be a ground reference terminal. The ground reference terminal of the logger-side terminal portion may be connected by a conductor of the data logger unit to a ground of the measurement module. One or more of the identification terminals of the sensor-side terminal portion may be electrically connected to the sensor ground reference terminal by a conductor of the sensor unit.

The reference potential may be a potential different from a ground potential of the measurement module.

The reference terminal of the sensor-side terminal portion may be a supply terminal. The reference terminal of the logger-side terminal portion may be a supply terminal. The supply terminal of the logger-side terminal portion may be electrically connected by a conductor of the data logger unit to a supply potential of the measurement module. One or more of the identification terminals of the sensor-side terminal portion may be electrically connected together and to the sensor supply terminal by a conductor of the sensor unit.

The sensor-side terminal portion may have a ground reference terminal. The logger-side terminal portion may have a ground terminal. The ground reference terminal of the logger-side terminal portion may be connected to a ground potential of the measurement module by a conductor of the data logger unit.

The characteristic property of the sensor unit may be determined by identification of a single terminal, among the identification terminals of the logger-side terminal portion, as having the reference potential. The identified terminal may correlate with the characteristic property.

The characteristic property of the sensor unit may be determined by identification of a set of terminals, among the identification terminals of the logger-side terminal portion, as having the reference potential. The set of identified terminals may correlate with the characteristic property.

The potentials of the identification terminals of the logger-side terminal portion may define a sequence of binary digits. The data logger unit may decode a value correlating with the characteristic property from the sequence of binary digits.

The sense elements may be provided to a flexible substrate of the sensor unit.

The flexible substrate may be elongate along an axis of elongation. The sense elements may comprise a plurality of conductive plates arranged along the axis of elongation of the flexible substrate.

The flexible substrate may be elongate along an axis of elongation. The sense elements may comprise one or more pairs of elongate conductive plates. Each pair of conductive plates may be arranged with one plate of the pair of conductive plates on one side of the axis of elongation and the other plate of the pair of conductive plates on the other side of the axis of elongation in a direction crossing the axis of elongation.

The sense elements may be arranged on one surface of the flexible substrate. A conductive region may be arranged on the other surface of the flexible substrate to the side on which the one or more pairs of conductive plates are arranged so as to underlie the sense elements.

The conductive plate may be connected, via a ground terminal of the sensor-side terminal portion, to a ground potential of the measurement module.

Prior to the measurement module performing the electrical measurement, the data logger unit may be removably attached to the sensor unit.

Subsequent to the measurement module performing the electrical measurement, the data logger unit may be detached from the sensor unit and attached to another sensor unit.

According to a second aspect of the present invention, there is provided a data logger unit for receiving data from a sensor unit provided to an absorbent article. The data logger unit comprises a logger-side terminal portion and a measurement module electrically connected to at least one measurement terminal of the logger-side terminal portion. The logger terminal portion is adapted for engagement with a sensor-side terminal portion of the sensor unit. The connection is to connect the sensor unit and the data logger unit together. The measurement module is arranged to perform an electrical measurement via the at least one measurement terminal of the logger-side terminal portion. The data logger unit has a plurality of identification terminals at the logger-side terminal portion. The plurality of identification terminals are electrically connected to the measurement module. The measurement module is configured to perform a measurement of the plurality of identification terminals. The measurement is performed to identify a characteristic property of the sensor unit. The characteristic property of the sensor unit is encoded in the electrical potentials of the identification terminals.

The logger-side terminal portion may have a reference terminal. The measurement module may be configured to provide a reference potential to the reference terminal of the logger-side terminal portion. The characteristic property of the sensor unit may be encoded in the potential at each of the identification terminals of the logger-side terminal portion as compared with the reference potential.

A resistor of the data logger unit may be electrically connected between each of the identification terminals of the logger-side terminal portion and a conductor of the data logger unit maintained at a potential provided by the measurement module which is different from the reference potential.

The reference potential may be a ground potential of the measurement module.

The reference terminal of the logger-side terminal portion may be a ground reference terminal. The ground reference terminal may be connected by a conductor of the data logger unit to a ground of the measurement module.

The reference potential may be a potential different from a ground potential of the measurement module.

The reference terminal of the logger-side terminal portion may be a supply terminal. The supply terminal may be electrically connected by a conductor of the data logger unit to a supply potential of the measurement module.

The logger-side terminal portion may have a ground terminal. The ground terminal of the logger-side terminal portion may be connected to a ground potential of the measurement module by a conductor of the data logger unit.

The characteristic property of the sensor unit may be determined by identification of a single terminal, among the identification terminals of the logger-side terminal portion, as having the reference potential. The identified terminal may correlate with the characteristic property.

The measurement module may be configured to determine the characteristic property of the sensor unit by identification of a set of terminals, among the identification terminals of the logger-side terminal portion, as having the reference potential. The set of identified terminals may correlate with the characteristic property.

The potentials of the identification terminals may define a sequence of binary digits. The data logger unit may decode a value correlating with the characteristic property from the sequence of binary digits.

The data logger unit may be detachably attachable to the sensor unit.

The data logger unit may be detachably attachable to the absorbent article.

The measurement module may be adapted to repeat performing the electrical measurement after the data logger unit is detached from the sensor unit and attached to another sensor unit.

According to a third aspect of the present invention, there is provided a sensor unit for an absorbent article for connection to a data logger unit to determine a hygiene state of the absorbent article. The sensor unit comprises a sensor-side terminal portion. The sensor unit comprises at least one sense element electrically connected to at least one measurement terminal of the sensor-side terminal portion. The sensor-side terminal portion is adapted for engagement with a logger-side terminal portion of the data logger unit. The engagement is thereby to connect the sensor unit and the data logger unit. The sensor terminal portion has a plurality of identification terminals at the sensor-side terminal portion. The identification terminals of the sensor-side terminal portion are configured to provide, by electrical measurement of the plurality of identification terminals, a characteristic property of the sensor unit. The characteristic property of the sensor unit is encoded in the electrical potentials of the identification terminals of the sensor-side terminal portion when connected to the data logger unit.

The sensor terminal portion may have a reference terminal. At least one of the identification terminals of the sensor-side terminal portion may be electrically connected via a conductor of the sensor to the reference terminal of the sensor-side terminal portion. The characteristic property of the sensor unit may be encoded in the potential at each of the identification terminals of the sensor-side terminal portion as compared with the reference potential.

One or more of the identification terminals of the sensor-side terminal portion may be electrically connected by a conductor of the sensor unit to the reference terminal of the sensor-side terminal portion. The remaining identification terminals of the sensor-side terminal portion may not be electrically connected to the sensor reference terminal.

The reference terminal of the sensor-side terminal portion may be a ground reference terminal. One or more of the identification terminals of the sensor-side terminal portion may be electrically connected together and to the ground reference terminal of the sensor-side terminal portion by a conductor of the sensor unit.

The reference terminal of the sensor-side terminal portion may be a supply terminal. One or more of the identification terminals of the sensor-side terminal portion may be electrically connected together and to the sensor supply terminal of the sensor-side terminal portion by a conductor of the sensor.

The sensor-side terminal portion may have a ground reference terminal.

The characteristic property of the sensor unit may be determined by identification of a single terminal, among the sensor identification terminals of the sensor-side terminal portion, as having the reference potential. The identified terminal may correlate with the characteristic property.

The characteristic property of the sensor unit may be determined by identification of a plurality of terminals of the sensor-side terminal portion, among the identification terminals of the sensor-side terminal portion, as having the reference potential. The set of identified terminals may correlate with the characteristic property.

The potentials of the identification terminals of the sensor-side terminal portion may define a sequence of binary digits. The sequence of binary digits may decode to a value correlating with the characteristic property.

The sense elements may be provided to a flexible substrate.

The flexible substrate may be elongate along an axis of elongation. The sense elements may comprise a plurality of conductive plates arranged along the axis of elongation of the flexible substrate.

The flexible substrate may be elongate along an axis of elongation. The sense elements may comprise one or more pairs of elongate conductive plates, each pair of conductive plates being arranged with one plate of the pair of conductive plates on one side of the axis of elongation, and the other plate of the pair of conductive plates on the other side of the axis of elongation in a direction crossing the axis of elongation.

The sense elements may be arranged on one surface of the flexible substrate. A conductive region may be arranged on the other surface of the flexible substrate to the side on which the one or more pairs of conductive plates are arranged so as to underlie the sense elements.

The conductive plate may be connected to a ground terminal of the sensor-side terminal portion.

The sensor unit may be detachably attachable to the data logger unit.

The sensor unit may be detachably attachable to the absorbent article.

The sensor unit may be configured to detect the presence of body fluids in an absorbent article in proximity to the sensor unit in a non-contact manner.

According to a fourth aspect of the present invention, there is provided a plurality of interchangeable sensor units according to the third aspect. Each sensor unit of the plurality of interchangeable sensor units has a common configuration of sensor-side terminal portion. The sensor-side terminal portion is adapted for engagement with a logger-side terminal portion of a common data logger unit. The engagement is such that the sensor units may be exchanged in connection with the data logger unit. The characteristic property may be a characteristic property which differs among the interchangeable sensor units. The characteristic property may be uniquely specified by the electrical potentials of the identification terminals of the sensor-side terminal portion of each sensor unit when connected to the data logger unit.

The characteristic property may be a length in an elongate direction of the sensor unit.

The characteristic property may be an electrical property associated with the at least one sense element.

The at least one sense element may comprise two elongate sense elements arranged parallel to one another. The characteristic property may be a capacitance between the sense elements.

The characteristic property may be a dimension associated with the at least one sense element.

The plurality of interchangeable sensor units may be adapted for detachable attachment to the common data logger unit.

According to a fourth aspect of the present invention, there is provided an absorbent article management system. The absorbent article management system comprises a data logger unit according to the second aspect. The absorbent article management system comprises a sensor unit according to the third aspect. The sensor unit is provided to an absorbent article such that the at least one sense element is arranged to determine a hygienic state of the absorbent article. The data logger unit is adapted to perform the method of the first aspect in a state in which the data logger unit is connected to the sensor unit. The data logger unit periodically performs an electrical measurement of the at least one sense element via the at least one measurement terminal of the sensors-side terminal portion and the at least one measurement terminal of the logger-side terminal portion. The data logger unit may associate information about the result of the electrical measurement with information about the electrical potential of the identification terminals of the sensor-side terminal portion for identifying the characteristic property of the sensor unit.

The data logger unit may comprise a data storage unit. The data logger unit may be adapted to store information about the result of the electrical measurement in association with information for identifying the characteristic property of the sensor unit.

The absorbent article management system may further comprise a remote terminal. The data logger unit may comprise a communication unit adapted to transmit data to the remote terminal. The communication unit may be adapted to transmit information about the result of the electrical measurement to the communication unit in association with information for identifying the characteristic property of the sensor unit.

The remote terminal may comprise a database. The database may be adapted to store information about the result of the electrical measurement in association with information for identifying the characteristic property of the sensor unit.

The data logger unit may be adapted to decode the electrical potentials of the identification terminals of the logger-side terminal portion to provide information about the characteristic property.

The remote terminal may be adapted to decode the electrical potentials of the identification terminals of the logger-side terminal portion to provide information about the characteristic property.

BRIEF DESCRIPTION OF THE DRAWINGS

For a better understanding of the present invention, and to show how the same may be carried into effect, reference will now be made, by way of example, to the accompanying drawings, in which.

DETAILED DESCRIPTION OF THE INVENTION

Figure 1:
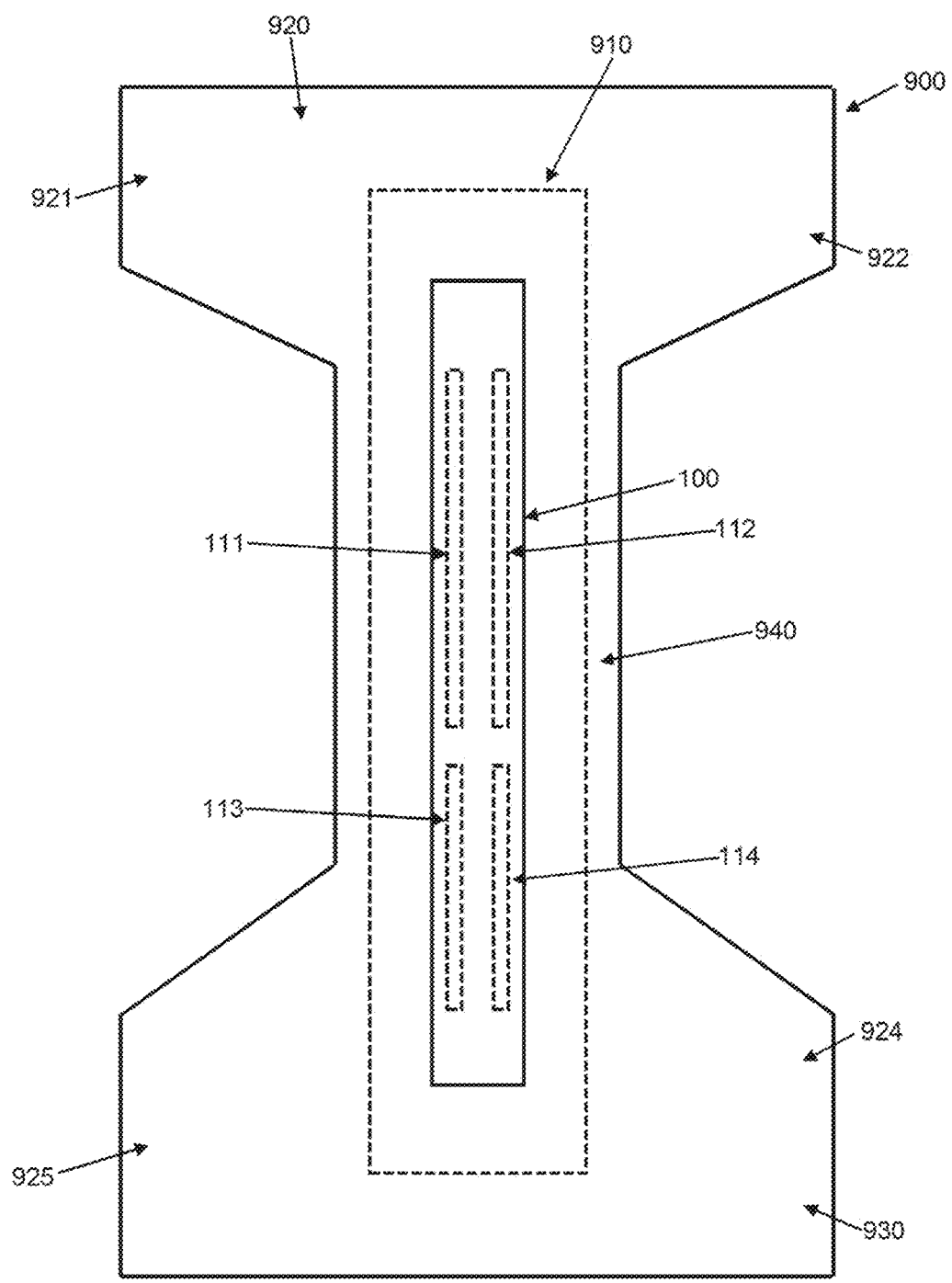
FIG. 1 shows an absorbent article to which a sensor unit being an embodiment of the present invention is provided.

FIG. 1 shows an exemplary configuration of an absorbent article 900, specifically a diaper. Diaper 900 has front port waist portion 920, rear waist portion 930, and crotch portion 940 connecting the front waist portion 920 to the rear waist portion 930. Diaper 900 has an outer surface which faces away from the user, when worn, and an inner surface, which faces toward the user, when worn.

In the configuration of diaper 900 shown in FIG. 1, front waist portion has tab portions 921 and 922 which are adapted to engage with corresponding tab portions 924 and 925 provided to rear waist portion 930. For example, tab portion 921 and 922 may be provided with adhesive regions, are arranged to adhere to adhesive regions provided to tab portion 924 and 925. Thereby, a secure fit of the diaper 900 around the waist of the user may be assured.

Diaper 900 also has an absorbent core 910 which is configured to absorb liquid and/or solid insults to the diaper from the user when worn. The construction of such a core, and the construction of the remainder of the diaper, may be conventional as known in the art. For example, the core may contain, in an absorbent layer, an absorbent material such as super-absorbent polymer, alone or in combination with further constituents, such as cellulosic fibers, and may comprise one or more additional layers having functions such as liquid acquisition, liquid distribution, and leakage prevention.

Diaper 900 may have a liquid permeable top sheet on its inner surface which provides a soft covering to the core 910. Diaper 900 may have a liquid impermeable backsheet on its outer surface to prevent leakage, and the absorbent core 910 disposed between the liquid permeable topsheet and the liquid impermeable backsheet. The construction of such diapers is well known in the art. It is noted that while the backsheet is typically liquid impermeable, it may, or may not, be vapour permeable, in other words breathable.

Diaper 900 is provided with sensor unit 100, the function of which is, in cooperation with appropriate measurement electronics, to sense the absorbent state, for example a wetness state, of the absorbent core 910. Sensor unit 100 is in the form of an elongate, flexible strip and is arranged to overly absorbent core 910. Sensor unit 100 has therefore, when arranged in a flat state, a longitudinal axis in the direction of elongation and a transverse axis in a direction across the axis of elongation, but in the plane of the strip. Sensor unit 100 need not be rectangular as shown, but can be bow-tie shaped, provided with curvilinear edges, can be oval, or can be another elongate shape.

Absorbent articles such as article 900 which are to be worn by the user or otherwise to be placed or secured on or against the user's body are conventionally understood to have an inside and an outside, the inside being the part which is, in use, to be arranged against the user's body, and the outside being the part which is to face outwardly of the user's body. As shown in FIG. 1, absorbent core 910 is on the inside of the absorbent article, while sensor unit 100 is provided on the outside of the absorbent article, here specifically on the side of the backsheet facing away from the absorbent core 910.

Sensor unit 100 may be fixed to the surface of absorbent article 900 by means of a layer of adhesive, by hook-and-loop fasteners, or by other methods of releasable or temporary attachment known in the art. Advantageously, sensor unit 100 is designed to be releasable from the absorbent article after it has been attached thereto, so that the same sensor unit may be reused with a number of different absorbent articles.

Sensor unit 100 is provided with sensing plates 111, 112, 113, 114, which act as the plates of a plane-parallel-plate capacitor. By measuring the impedance between pairs of plates 111, 112, 113, 114, the presence or absence of liquid in the absorbent core may be determined. Without wishing to be bound by theory, the presence of liquid in the absorbent core 910 modifies the dielectric constant of the region underlying sensor unit 100, and thereby modifies the dielectric constant of the space above, for example, plates 111 and 112, thereby affecting the impedance of the capacitor formed by those plates.

Such a configuration allows the detection of liquid in the absorbent core in a non-contact manner, in the sense that there is no direct contact between the body fluids and the sensor unit. Accordingly, sensor unit 100 can sense the state of an absorbent core or region of an absorbent core even when separated from the absorbent core by a liquid impermeable layer such as a liquid impermeable back sheet. This is in contrast, for example, to resistive-type sensing arrangements which tend to require contact between the liquid in the absorbent core and conductors which act as sense elements.

Figure 2:
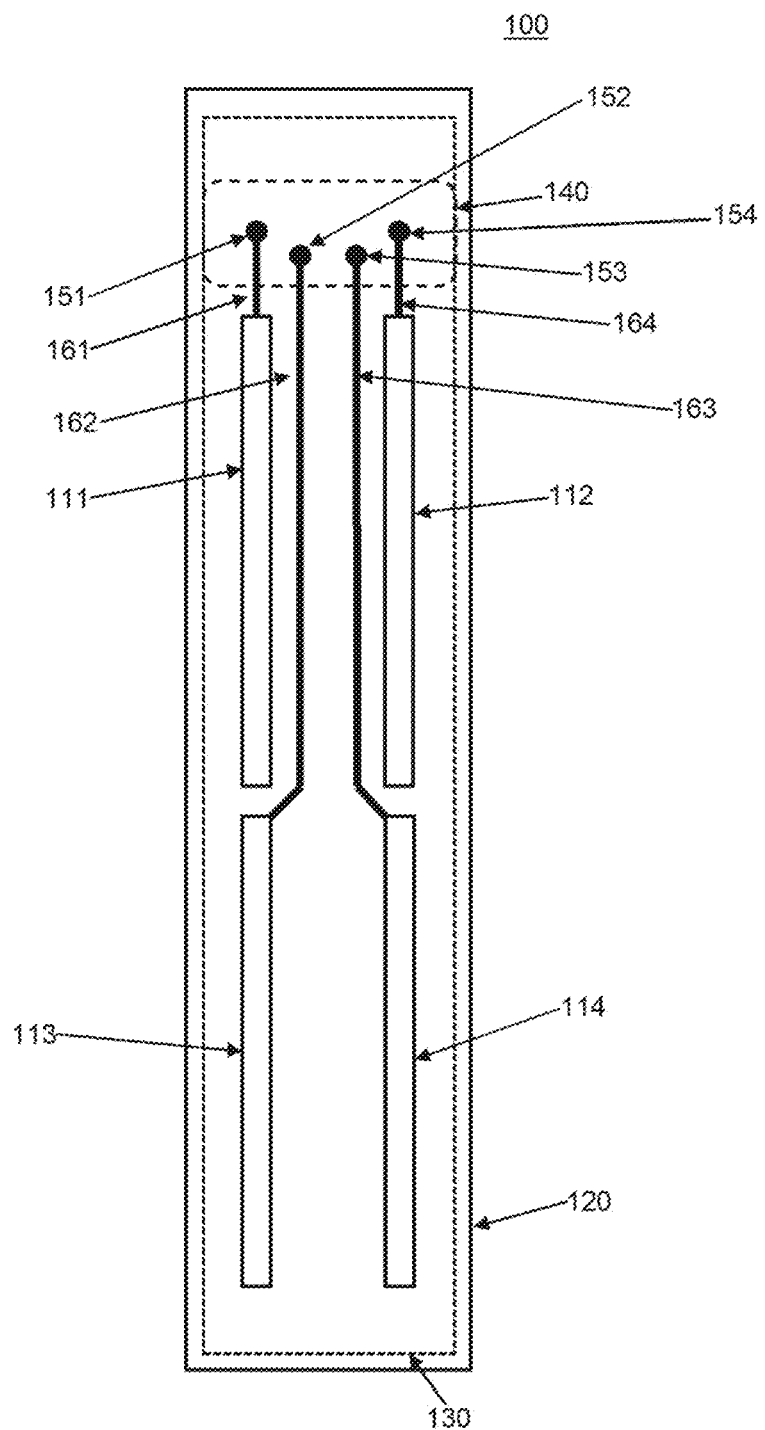
FIG. 2 shows a sensor unit being an embodiment of the present invention.

A more detailed view of an exemplary configuration of a sensor unit 100 is shown in FIG. 2, viewed from a side of the sensor unit at such that plates 111, 112, 113, 114 face the viewer. Sensor unit 100 has a flexible substrate 120 to which plates 111, 112, 113, 114 are provided, for example by surface plating. Flexible substrate 120, therefore, may be a flexible printed circuit board (flexible PCB).

On the side of flexible substrate 120 opposite to that having plates 111, 112, 113, 114 is grounding plate 130 which underlies substantially all of the surface of flexible substrate 120, but specifically that region which bears the plates 111, 112, 113, 114. Thereby, the influence on the impedances between the plates 111, 112, 113, 114 may predominantly be controlled by the environment above the surface of the flexible surface 120 carrying plates 111, 112, 113, 114, rather than on the environment adjacent to the opposite side of flexible substrate 120.

Each of plates 111, 112, 113, 114 is connected by a respective conductive trace 161, 162, 163, 164 to respective conductive pads 151, 153, 154 arranged in a terminal region 140 of the sensor unit.

Conductive traces 161, 162, 163, 164, as well as plates 111, 112, 113, 114 may be covered by a layer of dielectric material such a thin film on polymer. In contrast, pads 151, 152, 153, 154, are exposed at the surface of flexible substrate 120 so as to act as terminals facilitating connection between plates 111, 112, 113, 114 and measurement and data logging electronics, to be described later.

The configuration of plates may be varied. For example, more than two pairs of plates may be provided. The plates may be elongate as shown, but need not be. The plates may be rectangular as shown, but need not be. The plates may be provided in pairs arranged across the axis of elongation of the flexible substrate, but need not be. The plates may be parallel, or may be inclined one to another. A wide variation in the arrangement of plates and their respective positions on the flexible substrate may therefore be considered.

As can be appreciated from FIG. 1, it is advantageous if sensor unit 100 is adapted to the length of absorbent core 910 of diaper 900. For example, if sensor unit 100 is too long, the plates 111, 112, 113, 114 may overlie regions of the diaper 900 where liquid is not expected to be absorbed, and therefore the sensitivity may be reduced, or the influence of other components in diaper 900 may cause erroneous readings. In contrast, if sensor unit 100 is significantly shorter than absorbent core 910 in the longitudinal absorbent core 910 then liquid may accumulate in the absorbent core 910 at locations where sensor unit 100 cannot sense the presence of liquid.

Therefore, it is considered appropriate in some embodiments that sensor unit 100, or at least the part of it carrying the plates 111, 112, 113, 114, is coextensive and of comparable length and/or width as the absorbent core, for example, between 20% and 100% the respective dimension of the core, optionally between 30% and 80%, or further optionally between 40% and 60%. For example, a rectangle bounding the absorbent core 910 and a rectangle bounding the plates 111, 112, 113, 114, each in the flat state, may have comparable dimensions.

Moreover, with reference again to FIG. 1, the configuration of core 910 may be significantly more complex than that shown, and absorbent core 910 may comprise different regions having different absorbencies and/or difference widths. Accordingly, the layout of plates 111, 112, 113, 114 on sensor unit 100 may be adapted to such a configuration of absorbent core 910. In such embodiments, the plates may be arranged so as to be within the boundary of the absorbent core, but only to coextend with a particular location, such as a long-term storage region of the absorbent core.

Such adaption renders sensor unit 100 most effective only when used in conjunction which such absorbent cores. Sensor unit 100 may be ineffective when used in conjunction with absorbent cores of different configuration.

The most usual variation in absorbent core 910 results in a change in the size of diaper 900 to cope with different sizes of user, most commonly associated with different ages of user. Accordingly, a sensor unit 100 which is suitable for a use in conjunction with a diaper to be provided, for example, to a new-born infant is unlikely to be suitable for use in conjunction with a diaper to be provided, for example, to an adult male.

Accordingly, a proper selection of sensor unit 100 may depend closely on the absorbent article with which it is to be used. Therefore, if a plurality of different absorbent articles are to be provided in any particular situation, a corresponding plurality of corresponding sensor units 100 may also be provided. Each type of sensor unit 100 for use with a particular type of absorbent article 900 may differ in one of more characteristics from other sensor units of similar configuration. For example, the dimensions, particularly the length of the flexible substrate 120 may differ, and/or the positions and dimensions of the pads 111, 112, 113, 114. Also, the electrical properties of the sensor unit 100 may differ from other sensor units of similar configuration, for example, the capacitances or impedances between the plates measured in free space.

Importantly, the sensor unit 100 as shown in FIG. 2 is unable on its own to monitor the absorbent state of an absorbent article. To allow sensor unit 100 to monitor the absorbent state of an absorbent article, as shown in FIG. 3, sensor unit 100 is combined with a data logging unit 200 such that data logging unit 200 is able to supply electrical signals to sensor unit 100 and to measure changes in the electrical properties of the sensor unit 100.

Figure 3:
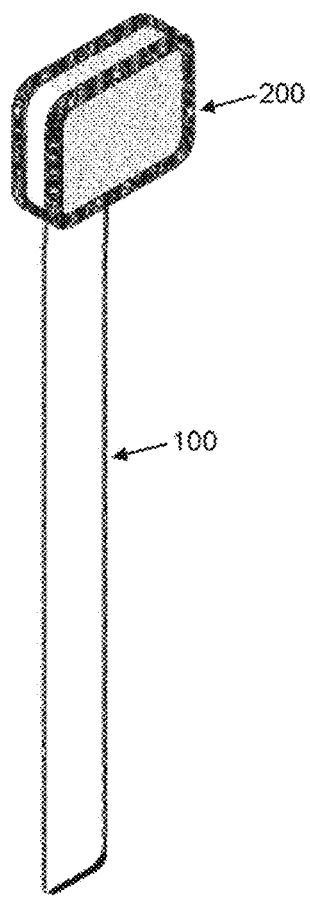
FIG. 3 shows a combination of a sensor unit and a data logging unit which is an embodiment of the present invention.
Figure 4:
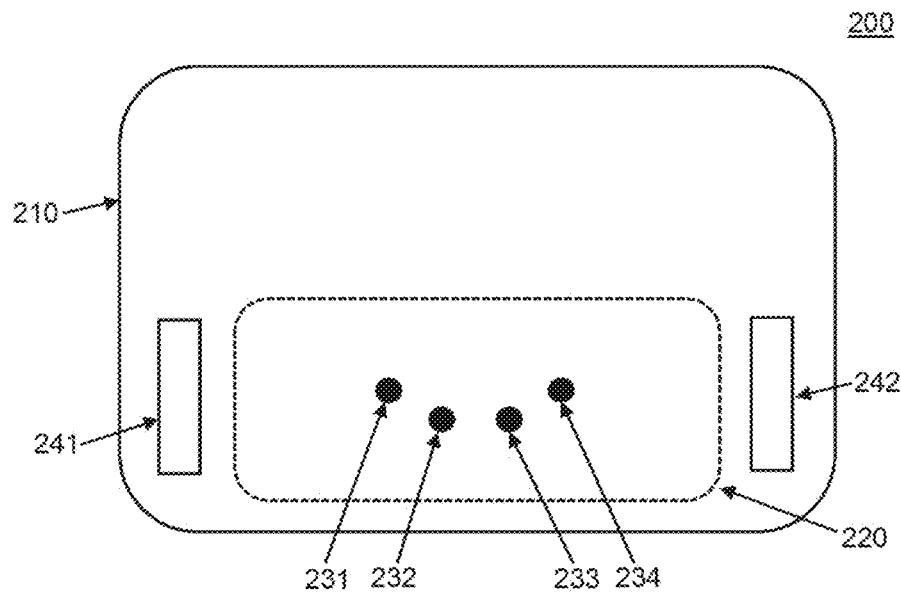
FIG. 4 shows a data logging unit which is an embodiment of the present invention with a terminal region exposed.

For example, in the configuration of FIG. 3, data logging unit may be configured to measure electric potentials between pairs of plates 111, 112, 113, 114 by means of pads 151, 152, 153, 154 provided in terminal region 140. An exemplary configuration of data logging unit 200 is shown in FIG. 4.

Data logging unit 200 shown in FIG. 4 has an enclosure 210 containing data logging electronics, to be described later.

At a terminal region 220 of enclosure 210, terminals 231, 232, 233, 234 are provided to correspond to pads 151, 152, 153, 154 of sensor unit 100 shown in FIG. 2. Terminals 231, 232, 233, 234 may be provided as, for example, spring terminals. Such spring terminal may be formed as flexible conductor plates projecting upwardly from terminal region 220 of enclosure 210 so as to form a good electric contact with a conductor pressed against the surface of enclosure 210 in which terminal region 220 is formed.

Such a terminal arrangement is here exemplary, and other terminal arrangements as known in the art will also be substitutable for the spring terminal according to their own suitability for a particular configuration. Such other terminal arrangements include, for example, mezzanine connectors, plug-and-socket connectors, registered jack or modular connectors, pogo-pin connectors, tip-ring-sleeve connectors, D-subminiature connectors, DIN connectors, or other terminal or connector types as known in the art. Where such connectors are gendered, either of the male part or the female part may be provided to data logging unit 200 and the other of the male part or the female part may be provided to sensor unit 100. Such terminal arrangements may also have a function to retain data logging unit 200 and sensor unit 100 in physical engagement as well as electrical connection, especially when locking or otherwise secured variants of such connectors are provided.

Terminal region 220 corresponds to terminal region 140 formed on sensor unit 110, in that the number and locations of terminals 231, 232, 233, 234 formed in terminal region 220 of data log 200 corresponds to the number and locations of pads 151, 152, 153, 154 of sensor unit 100. Accordingly, when terminal region 140 of sensor unit 100 is placed against terminal region 220 of data logging unit 200, data logging unit 200 may supply and measure electric signals associated with plates 111, 112, 113, 114 by terminals 231, 232, 233, 234 in order to perform measurements with sensor unit 100.

Figure 5:
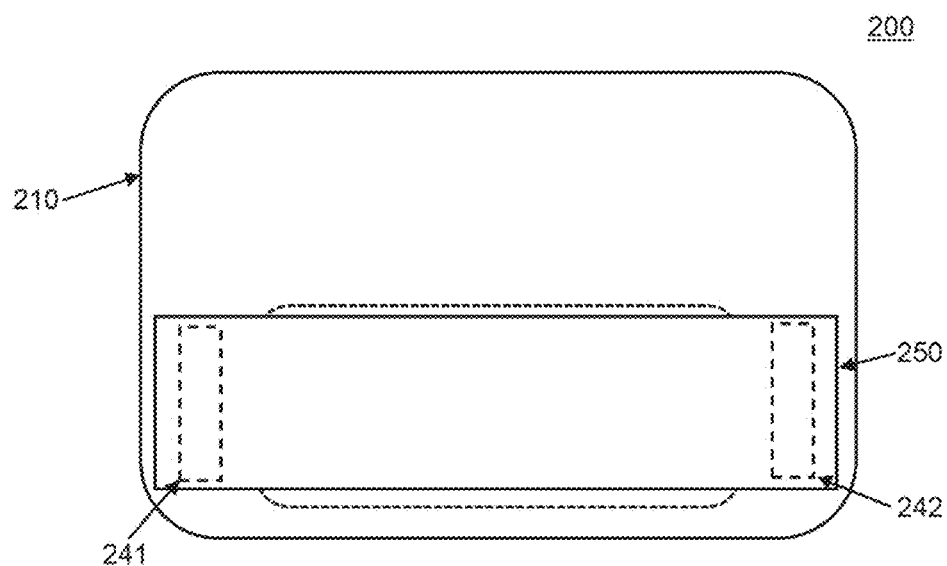
FIG. 5 shows a data logging unit which is an embodiment of the present invention with a terminal region covered by a clamp bar.

In order to secure terminal region 140 of sensor unit 100 against terminal region 220 of data logging unit 200, data logging unit 200 comprises an engagement element, here clamp plate 250, which has projections, not shown, which press-fit into apertures 241, 242, formed in enclosure 210. This configuration is shown in FIG. 5. By means of the press fit, clamp plate 250 applies force against terminal region 220, enabling clamp plate 250 to secure an interposed sensor strip.

Figure 6:
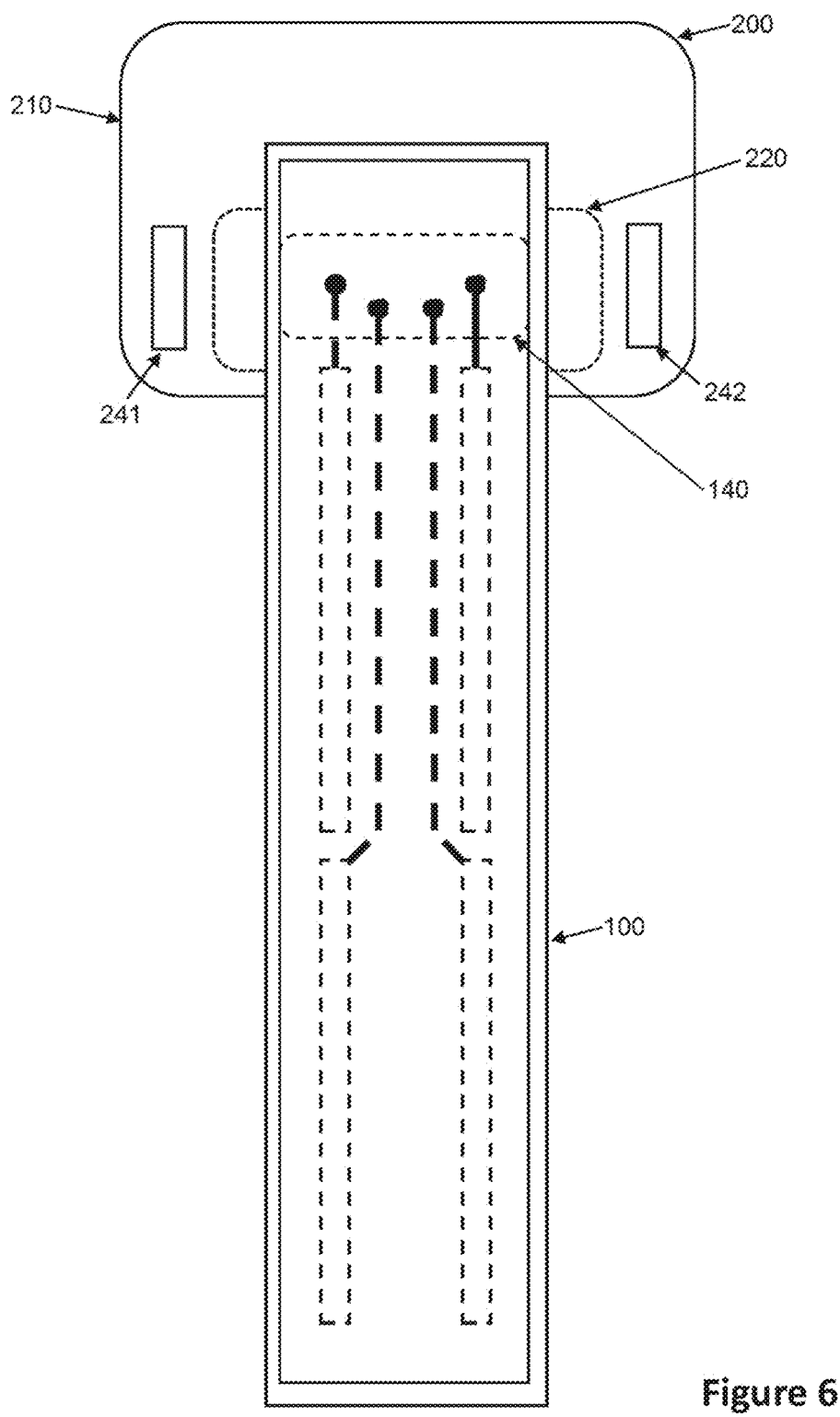
FIG. 6 shows a combination of a sensor unit and a data logging unit which is an embodiment of the present invention with aligned terminal regions.

To secure terminal region 140 of sensor unit 100 against terminal region 220 of data logging unit 200, and a configuration as shown in FIG. 6, may be adopted, wherein terminal region 140 of sensor unit 100 is placed against terminal region 220 such that terminals 231, 232, 233, 234 of data logging unit 200 align with pads 151, 152, 153, 154 of sensor unit 100.

Figure 7:
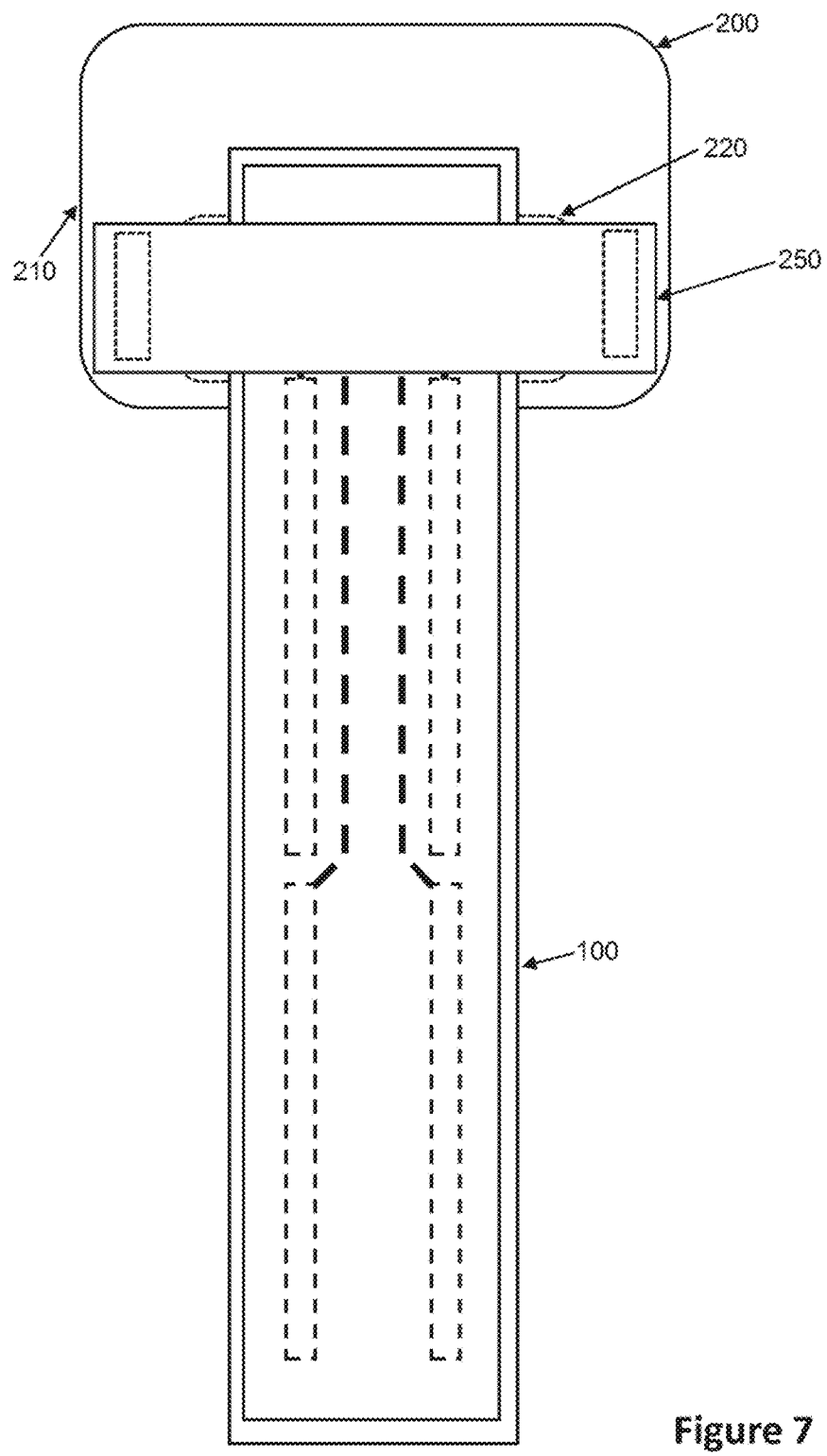
FIG. 7 shows a combination of a sensor unit and a data logging unit which is an embodiment of the present invention with terminal regions covered by a clamp bar.

Then, clamp plate 250 is provided to enclosure 210 such that the projections of clamp plate 250 engage with apertures (241, 242) of enclosure 210. The final configuration is shown in FIG. 7, in which clamp plate 250 secures terminal region 140 of sensor unit 100 against terminal region 220 of enclosure 210 sensor unit 100 is thereby appropriately secured and connected to data logging unit 200, such that data logging unit 200 can reliably send and obtain signals respectively to and from plates 111, 112, 113, 114 of sensor unit 100.

In order to correctly interpret the signals received from sensor unit 100, it is necessary to have information about the sensor unit 100 which is connected to data logging unit 200. In particular, different arrangements of plates and/or different dimensions of sensor unit 100 will give rise to different changes in impedance under different conditions in an absorbent article with which sensor unit 100 is provided.

However, the configuration of data logging unit 200 shown in FIG. 5, and particularly the configuration of terminal region 220 with associated terminals 231, 232, 233, 234 allows for a variety of sensor units 100 with a similarlyconfigured pads 151, 152, 153, 154 in terminal region 140, but having different configurations of plates 111, 112, 113, 114 to be used in conjunction with data logging unit 200.

It is possible for a user, a carer, or an operator of the system, to manually record which sensor 100 is associated with which a particular data logging unit 200, so that this information can be used to interpret the results from the data logging unit. However, it is advantageous if data logging unit 200 is able to obtain information about the sensor unit 100 to which it is connected such that this information is intermediately available, for use in further automated data-processing operations, and to avoid errors.

Accordingly, data logging unit 200 implements a method of identifying sensor unit 100 as will be further described in relation to FIGS. 8 to 15 below.

Figure 8:
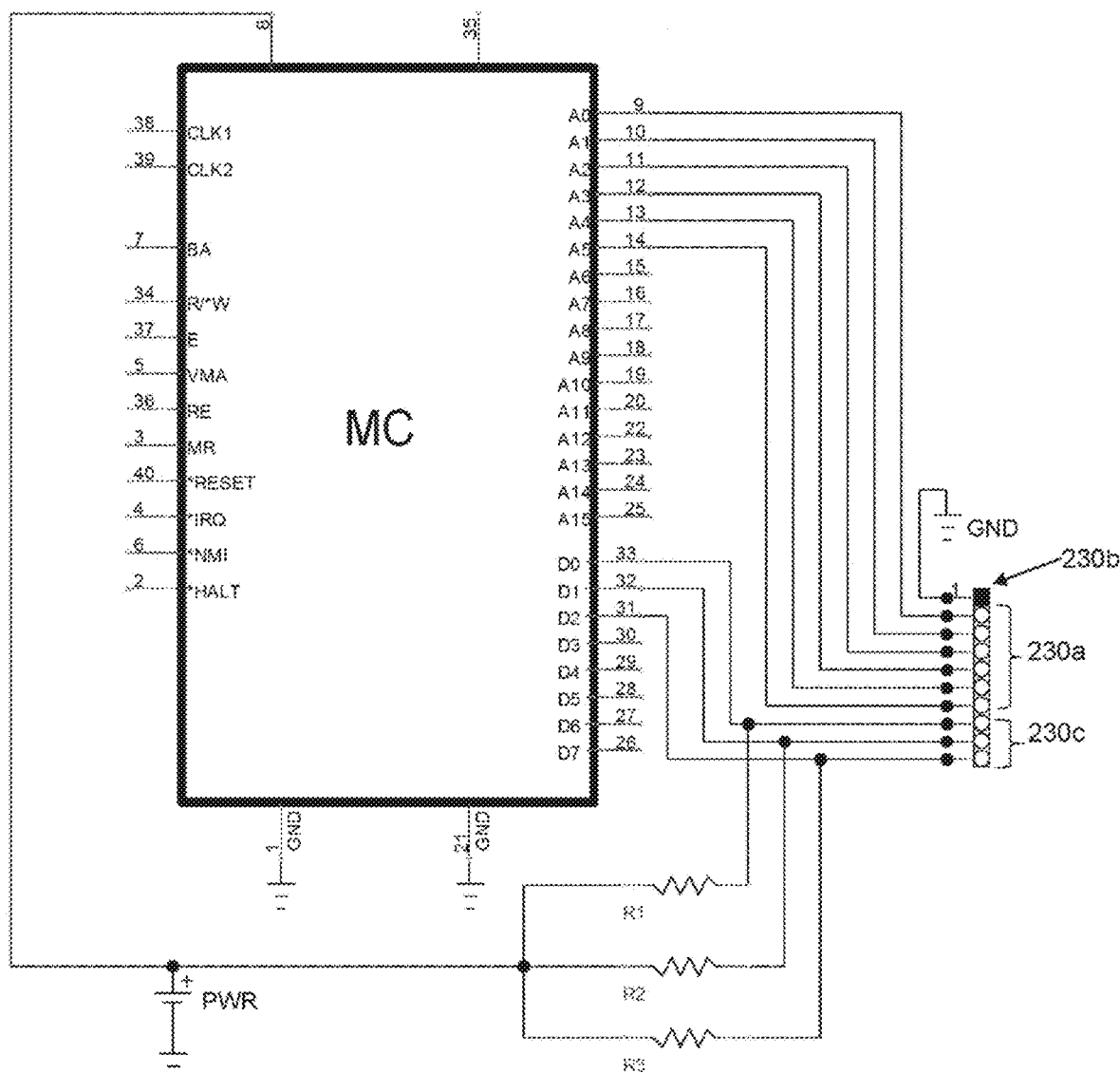
FIG. 8 shows a schematic electrical diagram of a data logging unit being an embodiment of the present invention.

Inside enclosure 210 of data logging unit 200 is provided a measurement unit MEAS which is schematically depicted in FIG. 8 as part of the overall data logging unit 200.

Measurement unit MEAS comprises microcontroller MC which has a plurality of analog measurement terminals A0 to A15 and a plurality of digital sense terminals D0 to D7. Microcontroller MC is supplied with power from power supply PWR, and has selected terminals of analog sense terminals A0 to A15 and digital terminals D0 to D7 connected, by means of conductive wiring, to a series of terminals 230 provided at terminal region 220 of enclosure 210.

Of these terminals, a subset of terminals 230a are connected to a subset of analog sense terminals A0 to A15, a subset of terminals 230c are connected to digital terminals D0 to D2, and one of the terminals 230b is connected to a ground GND of measurement unit MEAS.

In the configuration shown in FIG. 8, the digital terminals D0 to D7 of microcontroller MC, which are connected to terminals 230c of terminal region 220, are also connected individually to the power supply PWR by means of respective pull-up resistors R1, R2, R3. Accordingly, in an open-circuit state, terminals 230c are maintained at an elevated potential, corresponding to a logical HIGH or binary 1.

Terminals 230a, which are connected to the analog sense terminals A0 to A15 of microcontroller MC, are capable of being driven with potentials, for example, static or oscillating potentials, and are capable of performing measurements of potentials so as to measure simple or complex impedances between any of terminals 230a. Terminals 230a are thus referred to as measurement terminals.

Figure 9:
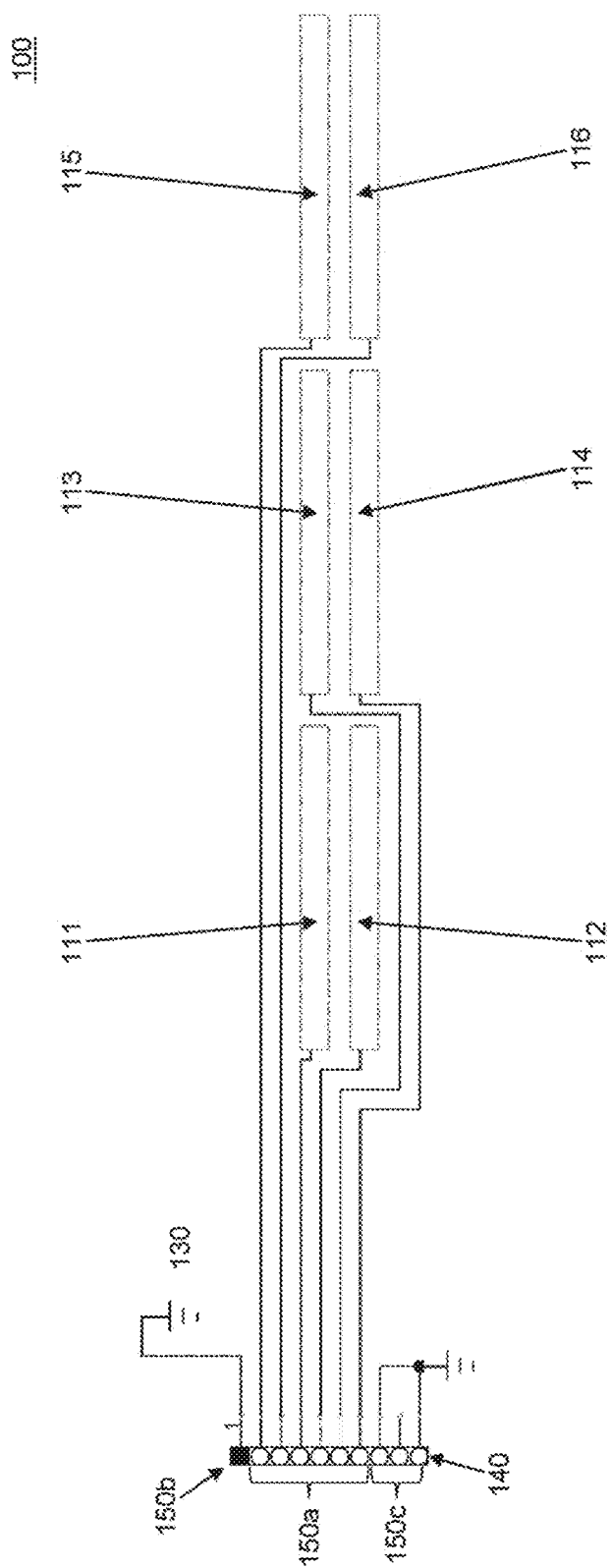
FIG. 9 shows a schematic electrical diagram of a sensor unit being an embodiment of the present invention.

For cooperation with the measurement unit 100 as shown in FIG. 8 and description in relation thereto, FIG. 9 shows a schematic diagram of the sensor unit 100. In the configuration shown in FIG. 9, six sense pads are provided, being pads 111, 112, 113, 114, 115, 116. As described above, the number and layout of the pads may be varied depending on the application.

Pads 111, 112, 113, 114, 115, 116 are connected by respective conductive traces to terminal region 140. In particular, of the terminals present at terminal region 140, a set of terminals 150a are individually connected to the respective pads 111, 112, 113, 114, 115, 116. These terminals 150a, as well as terminals 230a, are referred to as measurement terminals.

A terminal 150b is provided and connected to the grounding plate 130.

Finally, a set of terminals 150c are provided, of which a first and a third terminal in sequential order are connected to ground, and a second terminal is left unconnected. In other words, it is provided as an open circuit.

Accordingly, when sensor unit 100 shown in FIG. 9 is connected to a data logging 200 having a measurement unit MEAS as shown in FIG. 8, ground terminal 230b connects to ground terminal 150b, thereby to provide a reference ground from the sensor unit, sense terminals 230a connect to sense terminals 150a, thereby to allow measurement unit MEAS to measure impedances between selected pairs of pads 111, 112, 113, 114, 115, 116, and terminals 230c of data logging unit 200 connect to corresponding terminals 150c of sensor unit 100 such that the sequential first and third terminals 1 and 3 which are connected together at the sensor-unit-side, and which are moreover together connected to ground, reach a potential associated with ground, in other words, a digital LOW or binary 0 potential. In contrast, the sequential second terminal of terminals 230c, 150c is maintained at the digital high potential associated with power supply PWR by means of the action of pull-up resistor R2.

Of terminals 150c, the terminals which are connected to ground and the terminals which are left open determine the potentials, in terms of logical high or low potentials, which are detected at digital terminals D0 to D7 of microcontroller MC. These terminals may be used to identify a characteristic of the sensor strip 100 which is provided to data logging unit 200. Terminals 150c, as well as terminals 230c, therefore are referred to as identification terminals.

As shown in more detail in FIG. 10, for ease of comparison with later-described embodiments, the connection together or certain of identification terminals 150C may encode a binary number, for example, a binary triplet. Any of digital terminals D0 to D7 may be used for this purpose.

To demonstrate this, FIG. 9 shows a variant configuration in which a subset of terminals D5 to D7, instead of D0 to D2 are used for the identification of sensor 100.

Figure 10:
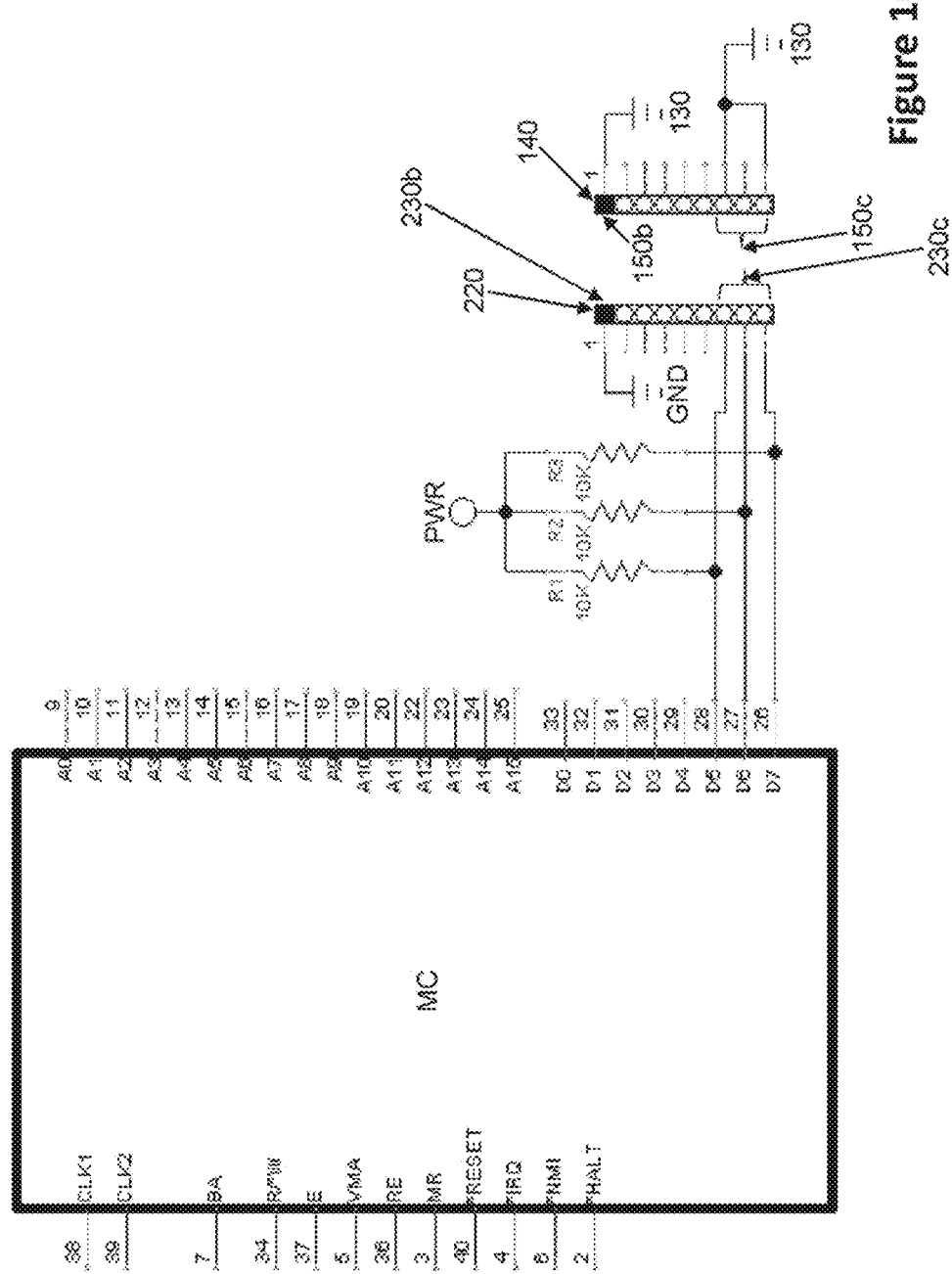
FIG. 10 shows a schematic electrical diagram of a data logging unit being a variant embodiment of the present invention.

In the configuration shown in FIGS. 9 and 10, the first and the third sequential identification terminals 150c are connected together and to ground, while the second sequential terminal is left as an open circuit. This may correspond to a sequence of binary digits 010, or in decimal notation 2 (two). Of course, in an alternative configuration, each of the first and third terminals could simply have an independent connection to ground.

Connecting together different terminals of identification terminals 150c and connecting these terminals to ground encodes different decimal numbers as a sequence of three binary digits. For example, the table below gives example possibilities for how a series of three binary digits presented on terminals 150c by means of connecting together certain terminals to ground to represent a digital LOW (or a binary 0), and leaving of certain terminals open to represent a digital HIGH (or a binary 1) could correspond to different lengths of sensor strip 100 suitable for different sizes types of absorbent article.

TABLE 1

| Binary Sequence | Decimal Equivalent | Size |
| --- | --- | --- |
| 000 | 0 | Test |
| 001 | 1 | Small adult |
| 010 | 2 | Medium adult |
| 011 | 3 | Large adult |
| 100 | 4 | Small baby |
| 101 | 5 | Medium baby |
| 110 | 6 | Large baby |
| 111 | 7 | No strip connected |

Accordingly, with only three terminals, eight states of the sensor strip can be identified, including the state in which no strip is connected. Moreover, no separate components are required on the sensor unit 100 side, and the identification encoding may be performed simply by connecting certain terminals 150c together, for example by conductive traces on flexible substrate 120.

Accordingly, the sensor strip is robust even under deformation, as compared with a situation where additional components may be provided on sensor strip on sensor unit 100 to provide identification signals.

A further variant configuration is shown in FIG. 11l, in which identification terminals 230c of terminal region 220 of data logger 200 are each individually connected to ground GND through a respective resistors R1, R2, R3 which therefore act as pull-down resistors. Also, selected identification terminals 150C of terminal region 140 of sensor unit 100 are connected together and are connected to a further terminal 150d, which corresponds with a terminal 230d of terminal region 220 of data logging unit 200 which is connected to the power supply. Terminals 230d and 150d may therefore be regarded as power supply terminals.

As a result of pull-down resistors R1, R2, R3, identification terminals 230C, when in the open-circuit state, are maintained as digital LOW (or a binary 0). However, when connected to identification terminals 150D which are connected together and, via power supply terminal 150C and power supply terminal 230D to the power supply PWR of data logging unit 200, the selected identification terminals 230C will be set to a potential corresponding to a digital HIGH (or a binary 1).

Again, in a similar manner as with regard to the embodiment variant of FIG. 10, the selection of which terminals are connected to the power supply potential, and which are left in the open-circuit state, may be used to encode a characteristic of sensor 100 which is connected to data logging unit 200.

Figure 12:
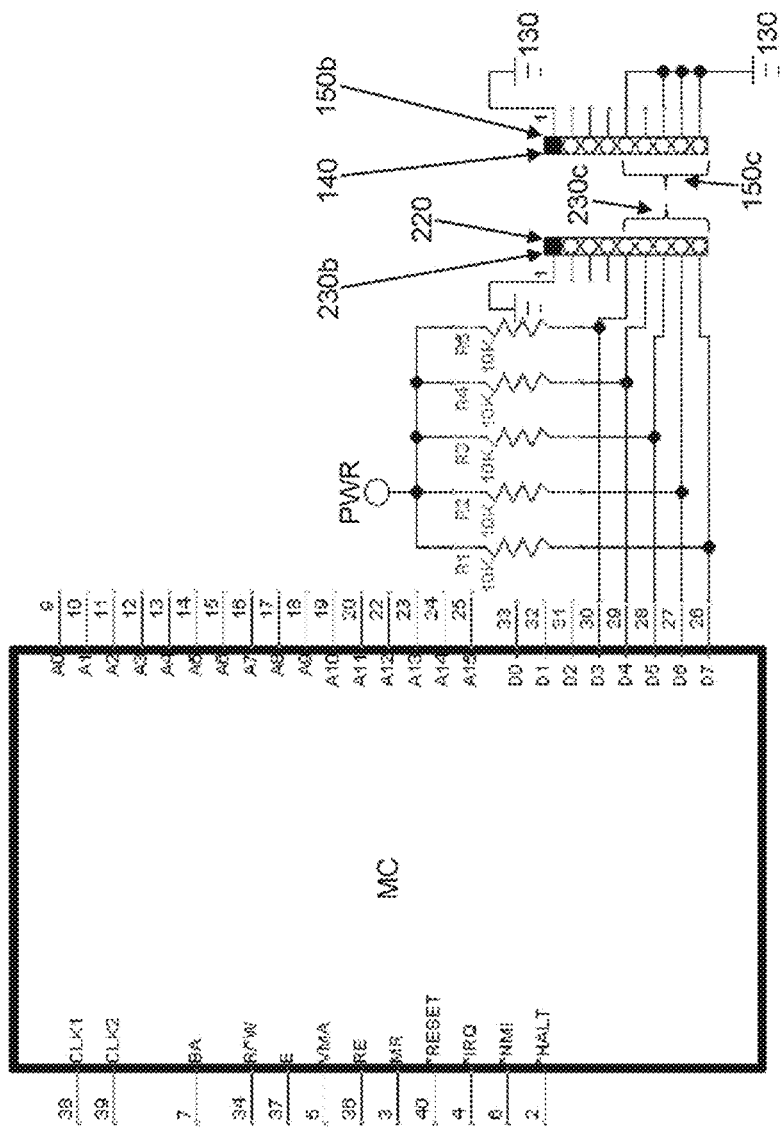
FIG. 12 shows a schematic electrical diagram of a data logging unit being another variant embodiment of the present invention.

In a further variant shown in FIG. 12, five digital terminals D3 to D7 are connected to five identification terminals 230c on terminal region 220 of data logging unit 200, and each of these terminals is individually connected to the power supply PWR via a respective resistor R1, R2, R3, R4, R5. Accordingly, R1, R2, R3, R4, R5 operate in a pull-up configuration.

On the sensor unit 100 side, a selected one of corresponding identification terminals 150c provided at terminal region 140 of sensor unit 100 is maintained in an unconnected state, while the remaining identification terminals 150c are connected to ground 130.

Rather than using a binary encoding, this configuration uses a numerical encoding, in which the sequential number of the terminal 150c which is not connected to ground encodes the type of sensor 100 which is connected. The decoding of the sensor type is simpler than the configuration of FIG. 12, but a greater number of identification terminals 230c is required to allow identification between a predetermined number of types of sensor unit 100 as compared with the binary encoding variants of FIGS. 10 and 11. For example, with eight terminals in the embodiment of FIG. 12, eight types of sensor unit 100 may be encoded, whereas with the variant of FIG. 10 or FIG. 11, 2^8 (two to the power of eight), or in other words 256 different configurations can be encoded with eight identification terminals.

Figure 13:
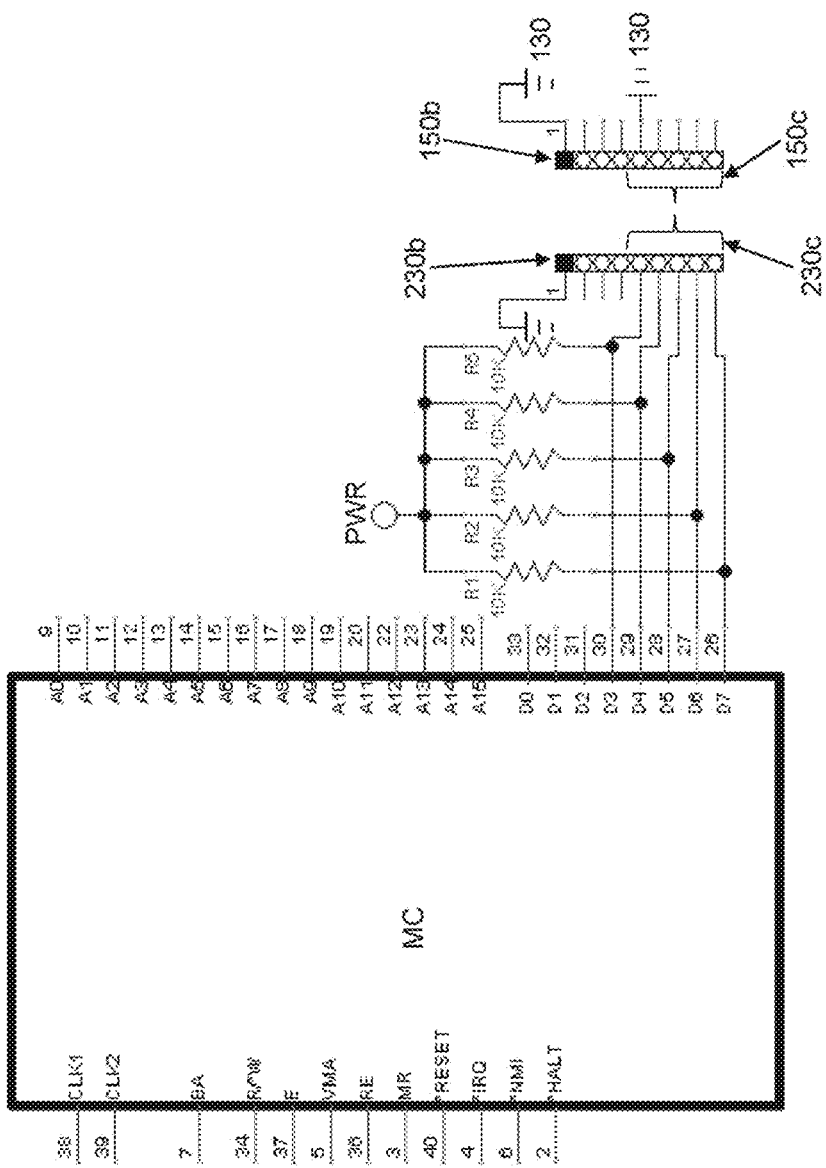
FIG. 13 shows a schematic electrical diagram of a data logging unit being another variant embodiment of the present invention.

A further variant is shown in FIG. 13, in which, rather than grounding all identification terminals 150c of sensor unit 100 except one, which is used to indicate the type of sensor unit 100 as in FIG. 12, in the embodiment of FIG. 13 all terminals 150c are left as open circuit, except one, which is grounded and thus used to indicate the characteristic of the sensor unit 100 which is attached.

Figure 11:
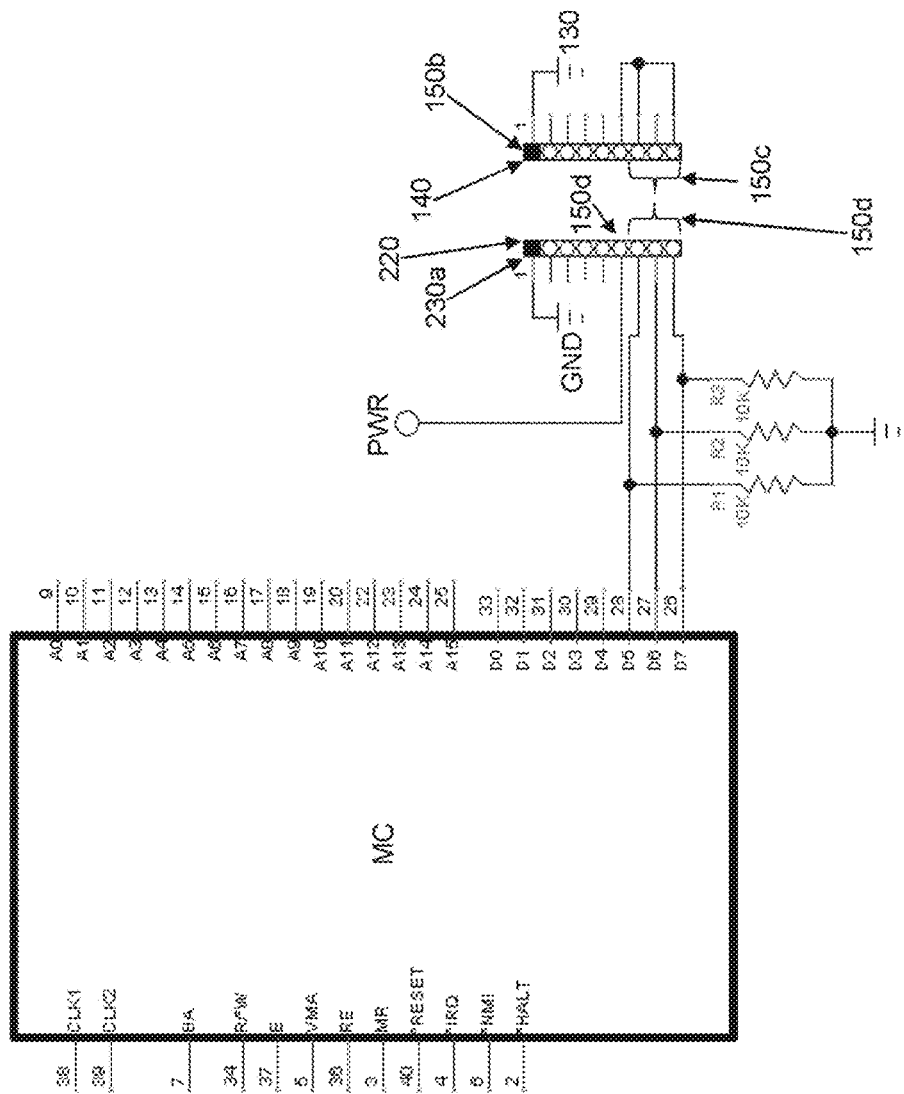
FIG. 11 shows a schematic electrical diagram of a data logging unit being another variant embodiment of the present invention.
Figure 14:
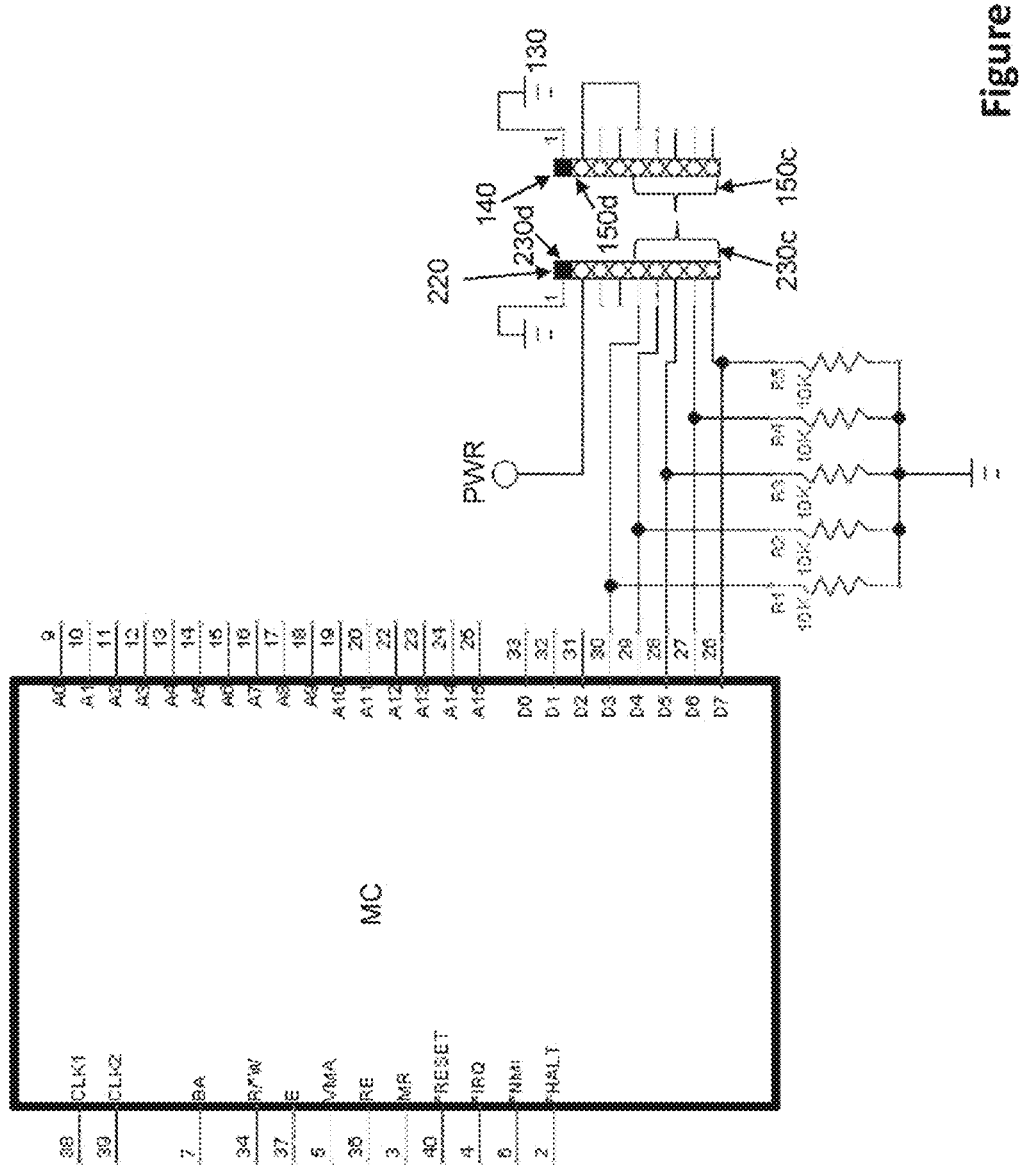
FIG. 14 shows a schematic electrical diagram of a data logging unit being another variant embodiment of the present invention.

A further configuration is shown in FIG. 14, as in the configuration of FIG. 11, a power connection to the power supply PWR of data logger 200 is provided at a power supply 230d terminal of terminal region 220 of data logging unit 220. Power supply terminal 230d is connected to power supply terminal 150d of terminal region 140 on sensor unit 140.

On the data-logging-unit side, identification terminals 220c are connected to ground via resistors R1, R2, R3, R4, R5, which function as pull-down resistors, while on the sensor-unit-side, a selected one of identification terminals 150c is connected via a conductive trace to power supply terminal 150d, while the other identification terminals are left as open circuit. Accordingly, the selected one of the identification terminals 150c is set at potential corresponding to digital HIGH, while the remaining identification terminals 150c are maintained at digital LOW. The selection of the terminal which is set as digital LOW encodes the characteristic of sensor 100 which is used.

Figure 15:
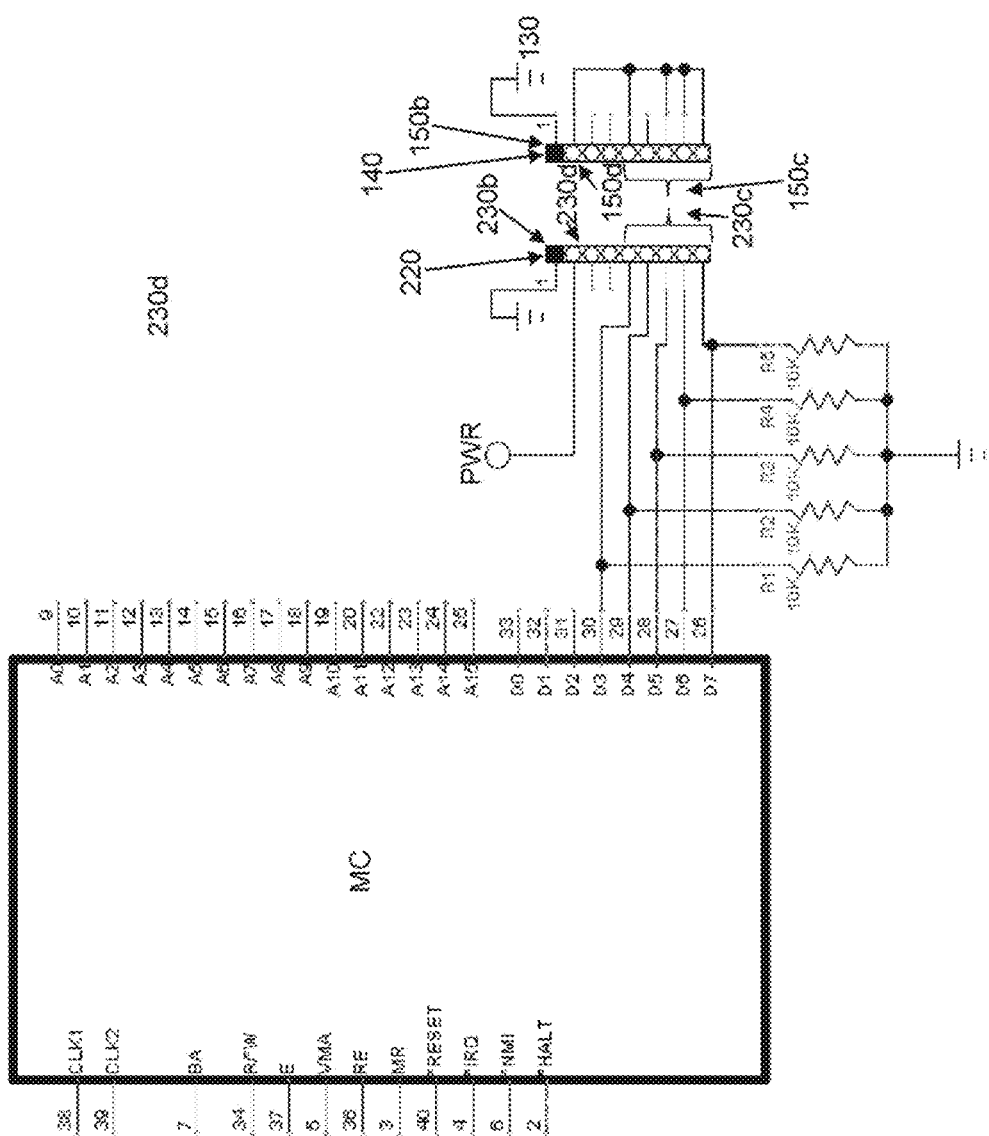
FIG. 15 shows a schematic electrical diagram of a data logging unit being another variant embodiment of the present invention.

A further variant is shown in FIG. 15, which corresponds to the configuration shown in FIG. 14, except that all identification terminals 150c on the sensor-unit-side are connected together and to power supply terminal 150d so as to correspond to a digital HIGH, except one, which is maintained at an open circuit. As a result, the selection of which terminal is maintained as an open circuit, corresponding to a digital LOW, encodes the type of sensor 100, which is connected.

In the above, disclosure has been made about a power supply PWR of the data logger 200. This may be a replaceable battery, a non-user replaceable battery, a rechargeable battery, a disposable battery, or any alternative power supply which would meet the needs of supplying a data logging unit as shown and described.

Enclosure 210 of data logging unit 200 may be, for example, a plastic enclosure, which may be sealed, or which may be openable to allow maintenance and adjustment, for example, replacement of the power supply.

In the above, description has been made about the identification of a sensor unit which measures the status of an absorbent article by means of sensing plates which act as plates of a capacitor, thereby to measure an inductance associated with the presence of liquid in the absorbent core of the absorbent article. However, the above disclosure is not limited to such a configuration, and may be used in connection with any type of sensor unit which may be used to measure the absorbent state of an absorbent article.

For example, it is envisaged that the disclosure set forth herein may be equivalently be applied in the sensors which may operate on a resistive basis, which may react to the presence of certain chemicals, or otherwise, and which may be applied to absorbent articles either by penetrating the absorbent core with sense elements or by other means of sensory association of sense elements with an absorbent core of an absorbent article.

Moreover, although the disclosure has been made in respect of diapers, the present disclosure is not so limited, and the techniques herein can be applied to sensors for the sensing of an absorbent state of another absorbent article, such as absorbent pads, pant-type diapers, belt-type diapers, incontinence shields, wound dressings, sanitary goods, such as sanitary napkins, without limitation.

In the above disclosure, the data logging unit may be a stand-alone data logging unit, which is equipped with the memory MRY and to which periodic measurements are stored. These periodic amendments may be later downloaded from the data logger to a management console, for example a personal computer, to evaluate a pattern of the absorbent state of the absorbent article over time. The data logging unit may be provided with a data retrieval interface such as a USB port for downloading over a wired connection, or may be provided with a short-range wireless data retrieval interface such as a Bluetooth module for downloading over a wireless configuration.

Alternatively, the data logging unit may measure the state of the absorbent article and may temporarily retain information about the state of the absorbent article in order to provide a notification on a change in the state of the absorbent article, for example by providing an audible (for example by a buzzer) or visible (for example by a light emitting diode, or LED) output signal from the data logging unit.

In another configuration, the data logging unit may be provided in association with a remote terminal, which may be a portable computing device such as a laptop, smartphone, or which may be a server or virtual server. The data logging unit may be connected by a wireless link to the remote terminal in order to periodically, on demand, or on detection on the change of absorbent status, signal the remote terminal in order to provide the results of the measurement to the remote terminal.

Figure 16:
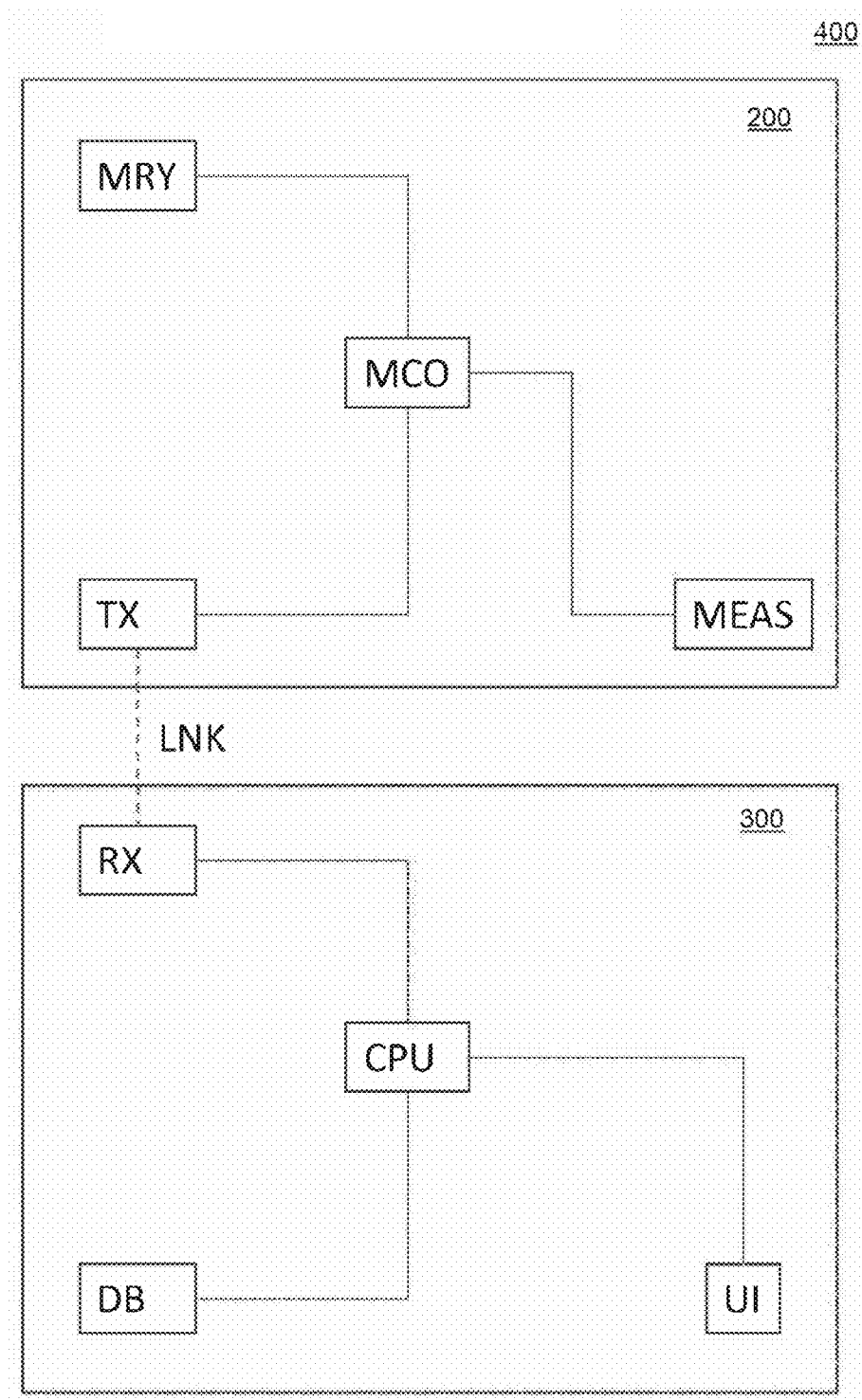
FIG. 16 shows a block diagram of a data logging unit and a remote terminal forming an absorbent article management system and being an embodiment of the present invention.

Such a configuration may be understood with reference to FIG. 16, in which data logging unit is provided, in addition to measurement unit MES, memory controller MCO, memory MRY, and transmission controller TX.

In the configuration of FIG. 16, data logger 200 may periodically make a measurement of the absorbent state of the absorbent article via the sensor unit 100. The result of this measurement may be recorded in a memory MRY by memory controller MCO. Then, according to a predetermined schedule, or when a predetermined number of measurements have been made, memory controller MCO may send the information stored in memory MRY, through transmission controller TX, to be transmitted on wireless link LNK to a reception controller RX of remote terminal 300.

Remote terminal 300 is provided with central processing unit CPU coupled to database DB and user interface UI. The data received from wireless link LNK by reception controller RX may be stored by the central processing unit CPU in database DB, which information may be retrieved by means of user interface UI.

Remote terminal 300 may be associated with a single data logging unit 200, or may be associated with a plurality of data logging units 200. In the former case, user interface controller UI may allow a user to query database DB to assess historical data on the absorbent status of the absorbent article associated with data logger 200. In the latter case, user interface controller UI may allow a user to query database DB to compare and analyse the results from a plurality of data loggers 200 associated with remote terminal 200.

In FIG. 16, data logger 200 and remote terminal 300 make up management system 400. In management system 400, memory MRY may be provided with a look-up table which enables measurement controller MCO to determine a characteristic of sensor unit 100 using the methods disclosed herein, such that the characteristic of sensor unit 100 may be stored together with the result of the measurement in memory MRY and may be transmitted together with the result of measurement to remote terminal 300 over wireless link LNK.

Alternatively, measurement unit MEAS may simply store the measurements of identification terminals 230c into memory MRY, which may be transmitted together with the measurement values over wireless link LNK. In such a configuration, database DB of the remote terminal 300 may include a look-up table enabling decoding of the identification information provided in identification terminals 230c so as to identify the characteristic of sensor unit 100 which is associated with the measurement.

In each of the above configurations, the measurement unit MEAS can determine the characteristic of the sensor unit 100 with each measurement made of the hygienic state of the absorbent article using sensor unit 100. In an alternative configuration, the determination may be performed once after a sensor unit 100 is connected to the data logger unit 200, which can be detected by a change in state of one of the identification terminals 230c.

The above disclosure has been made to specific examples, but one skilled in the art will appreciate that substantial modification and variation may be made without deviating from the various concepts in an advantageous configurations, devices, methods and systems herein disclosed and described. Accordingly, the present invention is to be understood as not being limited to the embodiments herein shown and described, but to be determined with reference to the appended claims.

What is claimed is:

1. A data logger unit for receiving data from a sensor unit provided to an absorbent article,
the data logger unit comprising a logger-side terminal portion and a measurement module electrically connected to at least one measurement terminal of the logger-side terminal portion, the logger terminal portion being adapted for engagement with a sensor-side terminal portion of the sensor unit thereby to connect the sensor unit and the data logger unit together;
the measurement module being arranged to perform an electrical measurement via the at least one measurement terminal of the logger-side terminal portion;
the data logger unit having a plurality of identification terminals at the logger-side terminal portion electrically connected to the measurement module;
the measurement module being configured to perform a measurement of the plurality of identification terminals to identify a characteristic property of the sensor unit; and
the characteristic property of the sensor unit being encoded in the electrical potentials of the identification terminals.

2. The data logger unit of claim 1,
the logger-side terminal portion having a reference terminal;
the measurement module being configured to provide a reference potential to the reference terminal of the logger-side terminal portion; and
the characteristic property of the sensor unit being encoded in the potential at each of the identification terminals of the logger-side terminal portion as compared with the reference potential.

3. The data logger unit of claim 1, wherein a resistor of the data logger unit is electrically connected between each of the identification terminals of the logger-side terminal portion and a conductor of the data logger unit maintained at a potential provided by the measurement module which is different from the reference potential.

4. The data logger unit of claim 1, wherein the reference potential is a ground potential of the measurement module.

5. The data logger unit of claim 4, wherein
the reference terminal of the logger-side terminal portion is a ground reference terminal; and
the ground reference terminal is connected by a conductor of the data logger unit to a ground of the measurement module.

6. The data logger unit of claim 1, wherein the reference potential is a potential different from a ground potential of the measurement module.

7. The data logger unit of claim 1, wherein
the reference terminal of the logger-side terminal portion is a supply terminal; and
the supply terminal is electrically connected by a conductor of the data logger unit to a supply potential of the measurement module.

8. The data logger unit of claim 7, wherein
the logger-side terminal portion has a ground terminal; and
the ground terminal of the logger-side terminal portion is connected to a ground potential of the measurement module by a conductor of the data logger unit.

9. The data logger unit of claim 7, wherein the characteristic property of the sensor unit is determined by identification of a single terminal, among the identification terminals of the logger-side terminal portion, as having the reference potential, the identified terminal correlating with the characteristic property.

10. The data logger unit of claim 1, wherein the measurement module is configured to determine the characteristic property of the sensor unit by identification of a set of terminals, among the identification terminals of the logger-side terminal portion, as having the reference potential, the set of identified terminals correlating with the characteristic property.

11. The data logger unit of claim 2, wherein the potentials of the identification terminals define a sequence of binary digits, and wherein the data logger unit decodes a value correlating with the characteristic property from the sequence of binary digits.

12. The data logger unit of claim 1, wherein the data logger unit is detachably attachable to the sensor unit.

13. The data logger unit of claim 1, wherein the data logger unit is detachably attachable to the absorbent article.

14. The data logger unit of claim 1, wherein the measurement module is adapted to repeat performing the electrical measurement after the data logger unit is detached from the sensor unit and attached to another sensor unit.

15. A sensor unit for an absorbent article for connection to a data logger unit to determine a hygiene state of the absorbent article,
the sensor unit comprising a sensor-side terminal portion and at least one sense element electrically connected to at least one measurement terminal of the sensor-side terminal portion;
the sensor-side terminal portion being adapted for engagement with a logger-side terminal portion of the data logger unit thereby to connect the sensor unit and the data logger unit;
the sensor terminal portion having a plurality of identification terminals at the sensor-side terminal portion;
the identification terminals of the sensor-side terminal portion being configured to provide, by electrical measurement of the plurality of identification terminals, a characteristic property of the sensor unit; and
the characteristic property of the sensor unit being encoded in the electrical potentials of the identification terminals of the sensor-side terminal portion when connected to the data logger unit.

16. The sensor unit of claim 15,
the sensor terminal portion having a reference terminal;
at least one of the identification terminals of the sensor-side terminal portion being electrically connected via a conductor of the sensor to the reference terminal of the sensor-side terminal portion; and
the characteristic property of the sensor unit being encoded in the potential at each of the identification terminals of the sensor-side terminal portion as compared with the reference potential.

17. The sensor unit of claim 16, wherein one or more of the identification terminals of the sensor-side terminal portion are electrically connected by a conductor of the sensor unit to the reference terminal of the sensor-side terminal portion, and the remaining identification terminals of the sensor-side terminal portion are not electrically connected to the sensor reference terminal.

18. The sensor unit of claim 16, wherein
the reference terminal of the sensor-side terminal portion is a ground reference terminal; and
one or more of the identification terminals of the sensor-side terminal portion are electrically connected together and to the ground reference terminal of the sensor-side terminal portion by a conductor of the sensor unit.

19. The sensor unit of claim 16, wherein
the reference terminal of the sensor-side terminal portion is a supply terminal; and
one or more of the identification terminals of the sensor-side terminal portion are electrically connected together and to the sensor supply terminal of the sensor-side terminal portion by a conductor of the sensor.

20. The sensor unit of claim 19, wherein
the sensor-side terminal portion has a ground reference terminal.

21. The sensor unit of claim 15, wherein the characteristic property of the sensor unit is determined by identification of a single terminal, among the sensor identification terminals of the sensor-side terminal portion, as having the reference potential, the identified terminal correlating with the characteristic property.

22. The sensor unit of claim 15, wherein the characteristic property of the sensor unit is determined by identification of a plurality of terminals of the sensor-side terminal portion, among the identification terminals of the sensor-side terminal portion, as having the reference potential, the set of identified terminals correlating with the characteristic property.

23. The sensor unit of claim 15, wherein the potentials of the identification terminals of the sensor-side terminal portion define a sequence of binary digits, and wherein the sequence of binary digits decodes to a value correlating with the characteristic property.

24. The sensor unit of claim 15, wherein the sense elements are provided to a flexible substrate.

25. The sensor unit of claim 24, wherein the flexible substrate is elongate along an axis of elongation, and wherein the sense elements comprise a plurality of conductive plates arranged along the axis of elongation of the flexible substrate.

26. The sensor unit of claim 25, wherein the flexible substrate is elongate along an axis of elongation, and wherein the sense elements comprise one or more pairs of elongate conductive plates, each pair of conductive plates being arranged with one plate of the pair of conductive plates on one side of the axis of elongation, and the other plate of the pair of conductive plates on the other side of the axis of elongation in a direction crossing the axis of elongation.

27. The sensor unit of claim 24, wherein the sense elements are arranged on one surface of the flexible substrate and a conductive region is arranged on the other surface of the flexible substrate to the side on which the one or more pairs of conductive plates are arranged so as to underlie the sense elements.

28. The sensor unit of claim 27, wherein the conductive plate is connected to a ground terminal of the sensor-side terminal portion.

29. The sensor unit of claim 15, wherein the sensor unit is detachably attachable to the data logger unit.

30. The sensor unit of claim 15, wherein the sensor unit is detachably attachable to the absorbent article.

31. The sensor unit of claim 15, wherein the sensor unit is configured to detect the presence of body fluids in an absorbent article in proximity to the sensor unit in a non-contact manner.

32. A plurality of interchangeable sensor units according to claim 15, each having a common configuration of sensor-side terminal portion being adapted for engagement with a logger-side terminal portion of a common data logger unit such that the sensor units may be exchanged in connection with the data logger unit, the characteristic property being a characteristic property which differs among the interchangeable sensor units, and which is uniquely specified by the electrical potentials of the identification terminals of the sensor-side terminal portion of each sensor unit when connected to the data logger unit.

33. The plurality of interchangeable sensor units according to claim 32, the characteristic property being a length in an elongate direction of the sensor unit.

34. The plurality of interchangeable sensor units according to claim 32, the characteristic property being an electrical property associated with the at least one sense element.

35. The plurality of interchangeable sensor units according to claim 34, the at least one sense element comprising two elongate sense elements arranged parallel to one another, the characteristic property being a capacitance between the sense elements.

36. The plurality of interchangeable sensor units according to claim 32, the characteristic property being a dimension associated with the at least one sense element.

37. The plurality of interchangeable sensor units according to claim 32, being adapted for detachable attachment to the common data logger unit.

38. An absorbent article management system comprising:
a data logger unit, comprising:
a logger-side terminal portion and a measurement module electrically connected to at least one measurement terminal of the logger-side terminal portion, the logger terminal portion being adapted for engagement with a sensor-side terminal portion of the sensor unit thereby to connect the sensor unit and the data logger unit together;
the measurement module being arranged to perform an electrical measurement via the at least one measurement terminal of the logger-side terminal portion;
the data logger unit having a plurality of identification terminals at the logger-side terminal portion electrically connected to the measurement module;
the measurement module being configured to perform a measurement of the plurality of identification terminals to identify a characteristic property of the sensor unit; and
the characteristic property of the sensor unit being encoded in the electrical potentials of the identification terminals;
a sensor unit comprising:
a sensor-side terminal portion and at least one sense element electrically connected to at least one measurement terminal of the sensor-side terminal portion;
the sensor-side terminal portion being adapted for engagement with a logger-side terminal portion of the data logger unit thereby to connect the sensor unit and the data logger unit;
the sensor terminal portion having a plurality of identification terminals at the sensor-side terminal portion;
the identification terminals of the sensor-side terminal portion being configured to provide, by electrical measurement of the plurality of identification terminals, a characteristic property of the sensor unit;
the characteristic property of the sensor unit being encoded in the electrical potentials of the identification terminals of the sensor-side terminal portion when connected to the data logger unit; and
the sensor unit being provided to an absorbent article such that the at least one sense element is arranged to determine a hygienic state of the absorbent article;
the data logger unit being adapted to perform the method of claim 1 in a state in which the data logger unit is connected to the sensor unit;
the data logger unit periodically performing an electrical measurement of the at least one sense element via the at least one measurement terminal of the sensors-side terminal portion and the at least one measurement terminal of the logger-side terminal portion and associating information about the result of the electrical measurement with information about the electrical potential of the identification terminals of the sensor-side terminal portion for identifying the characteristic property of the sensor unit.

39. The absorbent article management system according to claim 38, wherein the data logger unit comprises a data storage unit and wherein the data logger unit is adapted to store information about the result of the electrical measurement in association with information for identifying the characteristic property of the sensor unit.

40. The absorbent article management system according to claim 38, further comprising a remote terminal and wherein the data logger unit comprises a communication unit adapted to transmit data to the remote terminal, and wherein the communication unit is adapted to transmit information about the result of the electrical measurement to the communication unit in association with information for identifying the characteristic property of the sensor unit.

41. The absorbent article management system according to claim 40, wherein the remote terminal comprises a database and wherein the database is adapted to store information about the result of the electrical measurement in association with information for identifying the characteristic property of the sensor unit.

42. The absorbent article management system according to claim 38, wherein the data logger unit is adapted to decode the electrical potentials of the identification terminals of the logger-side terminal portion to provide information about the characteristic property.

43. The absorbent article management system according to claim 40, wherein the remote terminal is adapted to decode the electrical potentials of the identification terminals of the logger-side terminal portion to provide information about the characteristic property.

* * * * *